US012163180B2

(12) United States Patent
Lin et al.

(10) Patent No.: US 12,163,180 B2
(45) Date of Patent: Dec. 10, 2024

(54) PATTERNED FLOW-CELLS USEFUL FOR NUCLEIC ACID ANALYSIS

(71) Applicant: ILLUMINA, INC., San Diego, CA (US)

(72) Inventors: Shengrong Lin, Fremont, CA (US); Yir-Shyuan Wu, Albany, CA (US); Kevin Gunderson, Encinitas, CA (US); John A. Moon, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1135 days.

(21) Appl. No.: 17/010,675

(22) Filed: Sep. 2, 2020

(65) Prior Publication Data

US 2020/0399684 A1 Dec. 24, 2020

Related U.S. Application Data

(63) Continuation of application No. 14/304,556, filed on Jun. 13, 2014, now Pat. No. 10,787,698, which is a continuation of application No. 13/492,661, filed on Jun. 8, 2012, now Pat. No. 8,778,848.

(60) Provisional application No. 61/495,266, filed on Jun. 9, 2011.

(51) Int. Cl.
*C12Q 1/6806* (2018.01)
*C12Q 1/6837* (2018.01)
*G01N 27/447* (2006.01)

(52) U.S. Cl.
CPC ......... *C12Q 1/6806* (2013.01); *C12Q 1/6837* (2013.01); *G01N 27/447* (2013.01)

(58) Field of Classification Search
None
See application file for complete search history.

(56) References Cited

U.S. PATENT DOCUMENTS

| | | |
|---|---|---|
| 3,622,319 A | 11/1971 | Sharp |
| 4,727,027 A | 2/1988 | Wiesehahn et al. |
| 5,324,633 A | 6/1994 | Fodor et al. |
| 5,429,807 A | 7/1995 | Matson et al. |
| 5,436,327 A | 7/1995 | Southern |
| 5,451,683 A | 9/1995 | Barrett et al. |
| 5,482,867 A | 1/1996 | Barrett et al. |
| 5,491,074 A | 2/1996 | Aldwin et al. |
| 5,561,071 A | 10/1996 | Hollenberg et al. |
| 5,583,211 A | 12/1996 | Coassin et al. |
| 5,599,675 A | 2/1997 | Brenner |
| 5,624,711 A | 4/1997 | Sundberg et al. |
| 5,641,658 A | 6/1997 | Adams et al. |
| 5,658,734 A | 8/1997 | Brock et al. |
| 5,744,305 A | 4/1998 | Fodor et al. |
| 5,750,341 A | 5/1998 | Macevicz |
| 5,770,721 A | 6/1998 | Ershov et al. |
| 5,772,905 A | 6/1998 | Chou |
| 5,795,716 A | 8/1998 | Chee et al. |
| 5,831,070 A | 11/1998 | Pease et al. |
| 5,837,858 A | 11/1998 | Brennan |
| 5,856,101 A | 1/1999 | Hubbell et al. |
| 5,858,659 A | 1/1999 | Sapolsky et al. |
| 5,871,921 A | 2/1999 | Landegren et al. |
| 5,874,219 A | 2/1999 | Rava et al. |
| 5,919,523 A | 7/1999 | Sundberg et al. |
| 5,968,740 A | 10/1999 | Fodor et al. |
| 5,974,164 A | 10/1999 | Chee et al. |
| 5,981,185 A | 11/1999 | Matson et al. |
| 5,981,956 A | 11/1999 | Stern |
| 6,022,963 A | 2/2000 | McGall et al. |
| 6,025,601 A | 2/2000 | Trulson et al. |
| 6,033,860 A | 3/2000 | Lockhart et al. |
| 6,051,380 A | 4/2000 | Sosnowski et al. |
| 6,083,697 A | 7/2000 | Beecher et al. |
| 6,090,555 A | 7/2000 | Fiekowsky et al. |
| 6,124,120 A | 9/2000 | Lizardi |
| 6,136,269 A | 10/2000 | Winkler et al. |
| 6,171,730 B1 | 1/2001 | Kuroda et al. |
| 6,210,891 B1 | 4/2001 | Nyren et al. |
| 6,258,568 B1 | 7/2001 | Nyren |
| 6,266,459 B1 | 7/2001 | Walt et al. |
| 6,274,320 B1 | 8/2001 | Rothberg et al. |
| 6,287,768 B1 | 9/2001 | Chenchik |

(Continued)

FOREIGN PATENT DOCUMENTS

| | | |
|---|---|---|
| EP | 0 868 530 | 4/2003 |
| EP | 2159290 | 3/2010 |

(Continued)

OTHER PUBLICATIONS

Hahn et al., "Three-Dimensional Biochemical and Biomechanical Patterning of Hydrogels for Guiding Cell Behavior," Adv. Mater. 2006, 18:2679-2684. (Year: 2006).*
Andrews, et al., "Confining Light to Deep Subwavelength Dimensions to Enable Optical Nanopatterning", Science, vol. 324, No. 5929, May 25, 2009, 917-921.
Ayras, et al., "Multilevel structures in sol-gel thin films with a single UV-exposure using a gray-scale mask", Thin Solid Films, vol. 352, Sep. 8, 1999, 9-12.
Bains, et al., "A novel method for nucleic acid sequence determination", J. Theor Biol., 135(3), 1988, 303-307.
Bentley, et al., "Accurate whole human genome sequencing using reversible terminator chemistry", Nature, vol. 456, Nov. 2008, 53-59.

(Continued)

*Primary Examiner* — Kaijiang Zhang
(74) *Attorney, Agent, or Firm* — Dierker & Kavanaugh, P.C.

(57) ABSTRACT

Provided is a surface having metal regions and an interstitial region having a composition that differs from the metal regions, wherein a continuous gel layer coats the surface across the metal regions and the interstitial regions. Nucleic acids or other analytes can be attached to the continuous gel layer such that a greater amount is attached over the metal regions than over the interstitial region. Also provided are methods for making such surfaces. Methods are also provided for making an array of nucleic acids or other analytes using such surfaces.

19 Claims, 11 Drawing Sheets

(56) References Cited

U.S. PATENT DOCUMENTS

| | | | |
|---|---|---|---|
| 6,288,220 B1 | 9/2001 | Kambara et al. | |
| 6,291,183 B1 | 9/2001 | Pirrung et al. | |
| 6,291,193 B1 | 9/2001 | Khodadoust | |
| 6,297,006 B1 | 10/2001 | Drmanac | |
| 6,309,831 B1 | 10/2001 | Goldberg et al. | |
| 6,355,431 B1 | 3/2002 | Chee et al. | |
| 6,372,813 B1* | 4/2002 | Johnson et al. | G01N 33/54353 435/174 |
| 6,416,949 B1 | 7/2002 | Dower et al. | |
| 6,428,752 B1 | 8/2002 | Montagu | |
| 6,432,360 B1 | 8/2002 | Church | |
| 6,451,616 B1 | 9/2002 | Odom et al. | |
| 6,465,174 B1 | 10/2002 | Mirzabekov et al. | |
| 6,465,178 B2 | 10/2002 | Chappa et al. | |
| 6,482,591 B2 | 11/2002 | Lockhart et al. | |
| 6,489,606 B1 | 12/2002 | Kersey et al. | |
| 6,514,751 B2 | 2/2003 | Johann et al. | |
| 6,770,441 B2 | 8/2004 | Dickinson et al. | |
| 6,859,570 B2 | 2/2005 | Walt et al. | |
| 6,890,741 B2 | 5/2005 | Fan et al. | |
| 6,913,884 B2 | 7/2005 | Stuelpnagel et al. | |
| 6,932,934 B2 | 8/2005 | Choi et al. | |
| 6,986,989 B2 | 1/2006 | Mirkin et al. | |
| 7,019,835 B2 | 3/2006 | McMackin et al. | |
| 7,057,026 B2 | 6/2006 | Barnes et al. | |
| 7,106,513 B2 | 9/2006 | Moon et al. | |
| 7,115,400 B1 | 10/2006 | Adessi et al. | |
| 7,122,482 B2 | 10/2006 | Xu et al. | |
| 7,126,755 B2 | 10/2006 | Moon et al. | |
| 7,140,861 B2 | 11/2006 | Watts et al. | |
| 7,164,533 B2 | 1/2007 | Moon et al. | |
| 7,186,656 B2 | 3/2007 | Sreenivasan | |
| 7,205,244 B2 | 4/2007 | Stacey et al. | |
| 7,211,414 B2 | 5/2007 | Hardin et al. | |
| 7,244,559 B2 | 7/2007 | Rothberg et al. | |
| 7,279,113 B2 | 10/2007 | Watts et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,547,504 B2 | 6/2009 | Sreenivasan | |
| 7,582,420 B2 | 9/2009 | Oliphant et al. | |
| 7,595,883 B1 | 9/2009 | El Gamal et al. | |
| 7,635,445 B2 | 12/2009 | Choi et al. | |
| 7,785,526 B2 | 8/2010 | Voisin | |
| 7,785,790 B1 | 8/2010 | Church et al. | |
| 7,837,921 B2 | 11/2010 | Xu | |
| 2002/0012930 A1 | 1/2002 | Rothberg et al. | |
| 2002/0055100 A1 | 5/2002 | Kawashima et al. | |
| 2003/0036063 A1 | 2/2003 | Mirzabekov et al. | |
| 2003/0078314 A1 | 4/2003 | Johnson et al. | |
| 2003/0146145 A1 | 8/2003 | Krotz | |
| 2003/0170914 A1 | 9/2003 | Guire et al. | |
| 2003/0175702 A1 | 9/2003 | Schweitzer et al. | |
| 2004/0002090 A1 | 1/2004 | Mayer et al. | |
| 2004/0096853 A1 | 5/2004 | Mayer | |
| 2005/0053980 A1 | 3/2005 | Gunderson et al. | |
| 2005/0181440 A1 | 8/2005 | Chee et al. | |
| 2005/0191698 A1 | 9/2005 | Chee et al. | |
| 2005/0227252 A1 | 10/2005 | Moon et al. | |
| 2006/0006327 A1 | 1/2006 | Donaldson et al. | |
| 2006/0023310 A1 | 2/2006 | Putnam et al. | |
| 2006/0071075 A1 | 4/2006 | Moon et al. | |
| 2006/0102486 A1 | 5/2006 | Bentley et al. | |
| 2006/0119519 A1 | 6/2006 | Moon | |
| 2007/0099208 A1 | 5/2007 | Drmanac et al. | |
| 2007/0128624 A1 | 6/2007 | Gormley et al. | |
| 2007/0178516 A1 | 8/2007 | Sosnowski et al. | |
| 2007/0218610 A1 | 9/2007 | Lim et al. | |
| 2007/0237680 A1 | 10/2007 | Lee et al. | |
| 2008/0009420 A1 | 1/2008 | Schroth et al. | |
| 2008/0108082 A1 | 5/2008 | Rank et al. | |
| 2009/0026082 A1 | 1/2009 | Rothberg et al. | |
| 2009/0127589 A1 | 5/2009 | Rothberg et al. | |
| 2009/0186349 A1 | 7/2009 | Gunderson et al. | |
| 2010/0068490 A1 | 3/2010 | Shih et al. | |
| 2010/0111768 A1 | 5/2010 | Banerjee et al. | |
| 2010/0137143 A1 | 6/2010 | Rothberg et al. | |
| 2010/0239824 A1 | 9/2010 | Weitz et al. | |
| 2010/0282617 A1 | 11/2010 | Rothberg et al. | |
| 2011/0059865 A1 | 3/2011 | Smith et al. | |
| 2011/0105366 A1 | 5/2011 | Lebl et al. | |

FOREIGN PATENT DOCUMENTS

| | | |
|---|---|---|
| WO | 1989/10977 A1 | 11/1989 |
| WO | 1991/006678 A1 | 5/1991 |
| WO | 1993/017126 A1 | 9/1993 |
| WO | 1995/35505 | 12/1995 |
| WO | 1999/36576 | 7/1999 |
| WO | 2000/07022 | 2/2000 |
| WO | 2000/031148 A2 | 6/2000 |
| WO | 2000/053812 A2 | 9/2000 |
| WO | 2000/063437 A2 | 10/2000 |
| WO | 2001/001143 A2 | 1/2001 |
| WO | 2001/16370 | 3/2001 |
| WO | 01/62982 A2 | 8/2001 |
| WO | 2003/014392 A2 | 2/2003 |
| WO | 2004/018497 A2 | 3/2004 |
| WO | 2004/024328 | 3/2004 |
| WO | 2005/033681 | 4/2005 |
| WO | 2007/123744 A2 | 11/2007 |
| WO | 2008/093098 A2 | 8/2008 |

OTHER PUBLICATIONS

Dehlinger, et al., "Automated combinatorial process for nanofabrication of structures using bioderivatized nanoparticles", JALA 12, 267-76.

Drmanac, et al., "Accurate sequencing by hybridization for DNA diagnostics and individual genomics", Nature Biotechnology, 1998, 54-58.

Fodor, et al., "Light-Directed, Spatially Addressable Parallel Chemical Synthesis", Science, vol. 251, 1991, 767-773.

Hahn, et al., "Three-Dimensional Biochemical and Biochemical Patterning of Hydrogels for Guiding Cell Behavior", Advanced Materials 18, Oct. 17, 2006, 2679-2684.

Heller, et al., "Active microelectronic chip devices which utilize controlled electrophoretic fields for multiplex DNA hybridization and other genomic applications", Electrophoresis 21, 2000, 157-164.

Ito, et al., "Fabrication of sub-100 nm Patterns using Near Field Mask Lithography in Ultra-thin Resist Process", Journal of Photopolymer Science and Technology, 2005, 435-441.

Korlach, et al., "Selective aluminum passivation for targeted immobilization of single DNA polymerase molecules in zero-mode waveguide nanostructures", PNAS, vol. 105 No. 4, 2008, 1176-1181.

Levene, et al., "Zero-Mode Waveguides for Single-Molecule Analysis at high concentrations", Science 299, Jan. 31, 2003, 682-686.

Lin, et al., "Solution polymerization of acrylamide using potassium persulfate as an initiator: kinetic studies, temperature and pH dependence", European Polymer Journal 37, 2001, 1507-1510.

Lizardi, "Mutation detection and single-molecule counting using isothermal rolling-circle amplification", Nature Genetics, vol. 19, 1998, 225-232.

Lundquist, et al., "Parallel confocal detection of single molecules in real time", Opt. Lett. 33(9), 2008, 1026-1028.

Priyadarshi, et al., "Stop-flow lithography to generate cell-laden microgel particles", Lab on a Chip, vol. 8, No. 7, May 22, 2008, 1056-1061.

Reese, "Electronic Microarrays: Progress towards DNA Diagnostics" In: Microarray innovations: technology and experimentation, 2009, 207-224.

Ronaghi, M., et al., "A Sequencing Method Based on Real-Time Pyrophosphate", Science 281 (5375), Jul. 17, 1998, 363-365.

Ronaghi, M., "Pyrosequencing sheds light on DNA sequencing", Genome Res, 11(1), 2001, 3-11.

Ronaghi, M., et al., "Real-time DNA sequencing using detection of pyrophosphate release", Anal. Biochem. Nov. 1, 1996; 242 (1):84-9.

(56) References Cited

OTHER PUBLICATIONS

Shendure, et al., "Accurate Multiplex Polony Sequencing of an Evolved Bacterial Genome", Science, Sep. 9, 2005, 1728-1732.
Sosnowski, et al., "Rapid determination of single base mismatch mutations in DNA hybrids by direct electric field control", PNAS, 94, 1997, 1119-1123.
Thornton, "High Rate Thick Film Growth", Ann. Rev. Mater. Sci., 7, 1977, 239-260.

* cited by examiner

PATTERNED FLOW-CELLS USEFUL FOR NUCLEIC ACID ANALYSIS

This patent application is a continuation of U.S. patent application Ser. No. 14/304,556 filed on Jun. 13, 2014, which is a continuation of U.S. patent application Ser. No. 13/492,661 filed on Jun. 8, 2012, now U.S. Pat. No. 8,778,848, which claims priority to U.S. Provisional Patent Application No. 61/495,266 filed on Jun. 9, 2011, each of which is incorporated herein by reference in its entirety.

BACKGROUND

The present invention relates generally to genomics analysis, and more specifically to methods for producing arrays for high throughput genomics analysis.

The task of cataloguing human genetic variation and correlating this variation with susceptibility to disease stands to benefit from advances in genome wide sequencing methodologies. This cataloguing effort holds the promise for identifying the markers in each person's genome that will help medical professionals determine susceptibility of the individual to disease, responsiveness to specific therapies such as prescription drugs, susceptibility to dangerous drug side effects and other medically actionable characteristics. The cataloguing effort is well under way. This is due in large part to commercially available genome sequencing methodologies which are sufficiently cost effective to allow test subjects to be evaluated in a research setting. Improvements in sequencing methodologies are needed to accelerate the cataloguing effort. Perhaps even more significant is that the relatively high cost of sequencing has hindered the technology from moving beyond the research centers and into the clinic where doctors can obtain sequences for the general population.

Sequencing methodologies and the systems used to carry them out, exploit a complex collection of technologies. Improvements in some of these technologies have been shown to provide substantial cost reductions. However, it is difficult to predict which if any is amenable to cost reducing improvements. Given the dependencies between the technologies in the sequencing systems it is even more difficult to predict which can be modified without having an adverse impact on the overall performance of the methodology. Thus, there exists a need to identify improvements in sequencing methodologies and systems that can bring the promise of genomics research to the clinic where lives can be improved and in many cases saved. The present invention satisfies this need and provides related advantages as well.

BRIEF SUMMARY

The present disclosure provides a method of preparing a surface. The method can include the steps of (a) providing a surface having metal regions and interstitial regions, the interstitial regions having a composition that differs from the metal regions; (b) contacting the surface with a fluid including a polymerizable material, wherein the fluid coats the surface across the metal regions and the interstitial regions; and (c) polymerizing the polymerizable material, thereby forming a continuous gel layer that coats the surface across the metal regions and the interstitial regions, wherein portions of the gel layer that coat the metal regions have greater mass than portions of the gel layer that coat the interstitial regions.

In particular embodiments, a method of making a nucleic acid array is provided. The method can include the steps of (a) providing a surface having metal regions and interstitial regions, the interstitial regions having a composition that differs from the metal regions, wherein a continuous gel layer coats the surface across the metal regions and the interstitial regions; and (b) contacting the continuous gel layer with a fluid including nucleic acids under conditions wherein the nucleic acids become attached to the gel layer and wherein a greater amount of the nucleic acids from the fluid attach to portions of the gel layer that coat the metal regions than the amount of nucleic acids that attach to portions of the gel layer that coat the interstitial regions.

This disclosure provides a method of making a nucleic acid array. In particular embodiments, the method includes the steps of (a) providing a surface having metal regions and interstitial regions, the interstitial regions having a composition that differs from the metal regions, wherein a continuous gel layer coats the surface across the metal regions and the interstitial regions; (b) contacting the continuous gel layer with a fluid comprising nucleic acids; and (c) selectively modifying the portions of the gel layer that coat the interstitial regions compared to the portions of the gel layer that coat the metal regions, thereby attaching the nucleic acids to the gel layer, wherein a greater amount of the nucleic acids from the fluid attach to portions of the gel layer that coat the metal regions than the amount of nucleic acids that attach to portions of the gel layer that coat the interstitial regions.

Methods are provided for preparing a surface, including the steps of (a) providing a surface having mask regions and transparent regions, the mask regions having a composition that blocks transmittance of radiation in a first part of the electromagnetic radiation spectrum and transparent regions having a composition that transmits radiation in the first part of the electromagnetic radiation spectrum; (b) contacting the surface with a fluid comprising a photo-polymerizable material, wherein the fluid coats the surface across the mask regions and the transparent regions; and (c) selectively photo-polymerizing the portions of the fluid that coat the transparent regions compared to the portions of the fluid that coat the mask regions, thereby forming a gel that coats the transparent regions.

Also provided is a method of making a nucleic acid array. The method can include the steps of (a) providing a surface having mask regions and transparent regions, the mask regions having a composition that blocks transmittance of radiation in a first part of the electromagnetic spectrum and transparent regions having a composition that transmits radiation in the first part of the electromagnetic radiation spectrum, wherein a continuous gel layer coats the surface across the mask regions and the transparent regions; (b) contacting the continuous gel layer with a fluid including nucleic acids under conditions wherein the nucleic acids become attached to the gel layer and wherein a first subpopulation of the nucleic acids attach to portions of the gel layer that coat the mask regions and a second subpopulation of nucleic acids attach to portions of the gel layer that coat the transparent regions; and (c) irradiating the surface with radiation in the first part of the electromagnetic spectrum, thereby selectively modifying the nucleic acids of one of the subpopulations compared to the nucleic acids of the other subpopulation.

This disclosure further provides a method for preparing a surface that includes the steps of (a) providing a surface having mask regions and transparent regions, the mask regions having a composition that blocks transmittance of radiation in a first part of the electromagnetic radiation spectrum and transparent regions having a composition that transmits radiation in the first part of the electromagnetic radiation spectrum, the surface further including photo-reactive crosslinking reagents attached thereto; (b) contacting the surface with a fluid comprising a photo-polymerizable material, wherein the fluid coats the surface across the mask regions and the transparent regions; and (c) selectively irradiating the portions of the fluid that coat the transparent regions compared to the portions of the fluid that coat the mask regions, wherein the portions of the fluid that coat the transparent regions are photo-polymerized to form a gel and wherein the gel is photo-crosslinked to the surface at the transparent regions.

This disclosure further provides a nucleic acid array. The array can include a surface having metal regions and interstitial regions having a composition that differs from the metal regions, wherein a continuous gel layer coats the surface across the metal regions and the interstitial regions, wherein nucleic acids are attached to the continuous gel layer, and wherein a greater amount of the nucleic acids are attached to portions of the gel layer that coat the metal regions than the amount of nucleic acids that attach to portions of the gel layer that coat the interstitial region.

In particular embodiments, a nucleic acid array can have a surface with (a) mask regions or metal regions, wherein individual mask regions are attached to a single nucleic acid template; and (b) interstitial regions, wherein a continuous gel layer coats the surface across the mask regions and the interstitial regions, wherein a plurality of nucleic acid copies of the template nucleic acid are attached to the continuous gel layer in respective clusters surrounding the metal regions. The mask regions or metal regions can have a composition that blocks transmittance of electromagnetic radiation in a first part of the electromagnetic radiation spectrum and the interstitial regions can have a composition that transmits radiation in the first part of the electromagnetic radiation spectrum.

Also provided is a nucleic acid array having a surface with mask regions having a composition that blocks transmittance of electromagnetic radiation in a first region of the electromagnetic radiation spectrum and transparent regions having a composition that transmits radiation in the first part of the electromagnetic radiation spectrum, wherein a continuous gel layer coats the surface across the mask regions and the transparent regions, wherein nucleic acids are attached to the continuous gel layer, and wherein a greater amount of the nucleic acids are attached to portions of the gel layer that coat the transparent regions than the amount of nucleic acids that are attached to portions of the gel layer that coat the mask regions.

Further provided is a nucleic acid array having a surface with mask regions having a composition that blocks transmittance of electromagnetic radiation in a first part of the electromagnetic radiation spectrum and transparent regions having a composition that transmits radiation in the first part of the electromagnetic radiation spectrum, wherein a continuous gel layer coats the surface across the mask regions and the transparent regions, wherein nucleic acids are attached to the continuous gel layer, and wherein a greater amount of the nucleic acids are attached to portions of the gel layer that coat the mask regions than the amount of nucleic acids that are attached to portions of the gel layer that coat the transparent regions.

The methods and compositions are exemplified above in the context of embodiments that use a nucleic acid as an analyte. This is done for purposes of illustration and is not intended to be limiting. Rather any of a variety of analytes can be used in place of nucleic acids in the examples set forth above and throughout this disclosure. Exemplary analytes are set forth below.

DETAILED DESCRIPTION

Figure 1A:
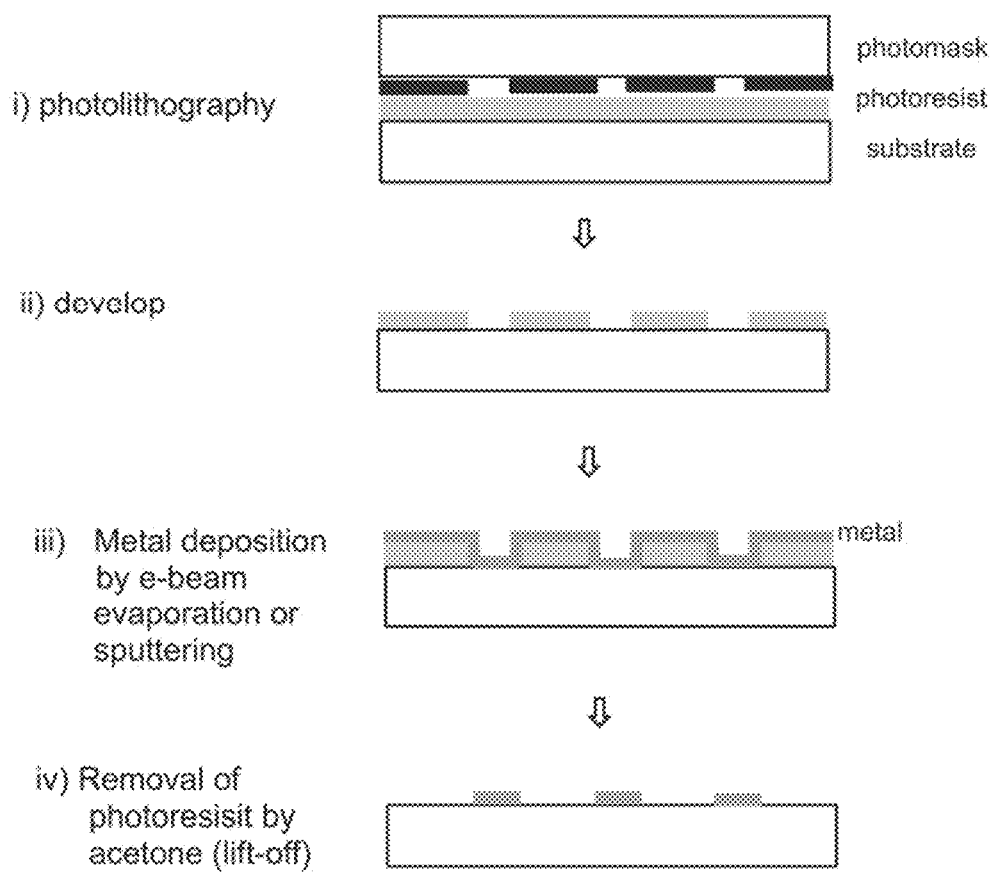
FIG. 1 shows diagrammatic representations of methods for making metal patterned surfaces using a combination of photolithography and metal layer deposition including a lift-off method (A), and an etch method (B).

The disclosure provides methods for coating a surface with a gel. Surprisingly, using methods set forth herein a greater mass of gel can be formed over a metal surface (such as a metal oxide) relative to the mass formed over another surface. Thus a method is provided in which a surface having a pattern of metal regions and interstitial regions is contacted with a polymerizable material and the material is polymerized to form a continuous gel layer that coats the surface such that portions of the gel layer that coat the metal regions have greater mass than portions of the gel layer that coat the interstitial regions.

This disclosure also provides methods for making an array of molecules attached to a surface. Particular embodiments exploit the surprising observation that a larger quantity of molecules can be attached to a portion of a gel layer that coats a metal surface relative to the quantity of molecules attached to a similar gel layer coating other surfaces. According to methods set forth in further detail below, a surface having a pattern of metal regions and interstitial regions covered by a continuous gel layer can be treated to attach molecules to the gel layer, the result of which is an array of the molecules present as features, the features corresponding to the portions of the gel layer that cover the metal regions.

In particular embodiments, a surface made in accordance with the methods set forth herein can be irradiated such that the metal regions act as a mask protecting portions of a gel layer, or molecules at the portions of the gel layer, that coat the metal regions. In contrast, portions of the gel layer that cover the interstitial regions, or molecules at those portions, are modified by the irradiation. For example, the gel layer can be irradiated to produce an array of gel portions having desired properties and corresponding to the shape and location of the metal regions. Similarly, the irradiation can be used to selectively ablate or remove molecules in the interstitial regions to leave an array of molecules corresponding to the shape and location of the metal regions. Metal oxides such as indium tin oxide and zinc oxide are particularly useful materials for a mask because the band gap for these masks is such that they absorb radiation in the UV range and transmit radiation in the visible range. Thus, metal oxide can form a mask that is useful in a process of making or modifying an array using UV range photo-reactions, but will not interfere with analytical applications of the array using detection in the visible range.

Embodiments of the invention are exemplified and described herein with reference to metal regions and interstitial regions that are located on a surface. However, the invention need not be limited such that the regions are on a surface. Rather in particular embodiments, a metal region, interstitial region or both can occur in a solid support or under the surface of the solid support. Furthermore, the location of a metal region, interstitial region or both can change with respect to a solid support. The change can be brought about by modifying the solid support, for example, by etching or polishing the solid support to bring a region to the surface from below. The change can be brought about by covering a region on a surface, by coating the surface or by building up the solid support.

Although several aspects of the invention are exemplified with respect to the use of metal as a mask, it will be understood that other materials appropriate to block radiation of a particular wavelength can also be used. Generally, a mask region on a surface, such as a metal region on a surface, can provide a near-field mask to selectively block irradiation of a particular wavelength. The near-field mask is generally located in a plane that is less than 1 wavelength from the surface (in the z-dimension) and therefore provides advantages in overcoming diffraction limits of other masking methods, such as those used in standard lithography techniques. Surprisingly, it has been observed that in the methods set forth herein a near-field mask is capable of protecting a gel layer and molecules attached to the gel layer from the effects, not only of collimated radiation, but also of non-collimated radiation. As set forth in further detail below, a near-field mask that is on a surface and used during an irradiation step for preparing the surface, or materials in contact with the surface, can be subsequently removed from the surface. Alternatively, the near-field mask can be retained on the surface for one or more other manipulation including, but not limited to, those manipulations set forth herein. The mask may influence one or more other manipulations carried out on or near the surface, but need not have any particular impact for any particular manipulation.

As used herein, the term "surface" is intended to mean an external part or external layer of a solid support. The solid support can be a rigid solid and optionally can be impermeable to liquids or gases. The solid support can also be a semi-rigid solid, for example, being permeable to liquids or gases. The surface can be in contact with another material such as a gas, liquid, gel, second surface of a similar or different solid support, metal, or coat. The surface, or regions thereof, can be substantially flat. The surface can have surface features such as wells, pits, channels, ridges, raised regions, pegs, posts or the like.

As used herein, the term "metal region" is intended to mean an area in a substrate or on a surface that contains a metal. A metal region can differ from another region with respect to the type of metal or quantity of a particular metal that is present at the metal region. The metal region can have a continuous coating of one or more type of metal. The metal region can have a composition and thickness that is sufficient to mask the transmittance of electromagnetic radiation from a particular part of the electromagnetic radiation spectrum including, for example, a part that is in the radio, microwave, infrared, visible, ultraviolet, X-ray or gamma ray parts of the spectrum. The metal can have a thickness in the range of 1 atom thickness to the thickness of a flow cell or other chamber where the metal coated surface resides. For example, the thickness of the metal can be at least about 1 nm, 5 nm, 10 nm, 50 nm, 100 nm, 250 nm or 500 nm. Alternatively or additionally, the thickness of the metal can be at most about 1 nm, 5 nm, 10 nm, 50 nm, 100 nm, 250 nm or 500 nm. The metal region can include, for example, aluminum, aluminum oxide, titanium, titanium oxide, zinc, zinc oxide, zinc sulfide, zinc selenide, boron or indium tin oxide. The metal region can include a Group I (alkali) metal, examples of which include, lithium (Li), potassium (K), rubidium (Rb), caesium (Cs) or francium (Fr). The metal region can include a Group II (alkaline earth metal) such as beryllium (Be), magnesium (Mg), calcium (Ca), strontium (Sr), barium (Ba) or radium (Ra). Also useful as a metal region are those that include a heavy metal halide, polycrystalline material such as lanthanum oxides, arsenic trisulfide, amorphous/polycrystalline silicon, silicon/germanium alloy, III-V semiconductor such as GaAs, or II-VI semiconductor such as CdS. Metals that form a dielectric stack or small interference mirror can be useful. In particular embodiments, a metal that is present at a metal region is positively charged. As evident from the examples above, a metal region can include a metal oxide.

As used herein, the term "mask region" is intended to mean an area in a substrate or on a surface having a composition and thickness that is sufficient to block the transmittance of electromagnetic radiation from a particular part of the electromagnetic radiation spectrum. In some but not all embodiments, the substrate or surface also has an interstitial region that is transparent to at least a portion of the particular part of the electromagnetic radiation spectrum that is blocked by the mask. The part of the electromagnetic radiation spectrum can include, for example, a part that is in the radio, microwave, infrared, visible, ultraviolet, X-ray or gamma ray parts of the spectrum. An exemplary mask region is a "near-field mask region" which is located such that the plane of the mask that is distal to the surface is less than about 1 wavelength distance from the surface (in the z-dimension). In particular embodiments a near field mask is used with electromagnetic radiation in the parts of the spectrum set forth above. Accordingly, the plane of the mask that is distal to the surface can be less than about 10 nm, 50 nm, 100 nm, 200 nm, 300 nm, 400 nm, or 500 nm from the surface. In particular embodiments, a metal region can function as a mask region or as a near-field mask region. As such, a mask region or near-field mask region can have a composition exemplified herein for metal regions.

As used herein, the term "interstitial region" is intended to mean an area in a substrate or on a surface that separates other areas of the substrate or surface. The term can refer to an area that separates other areas of a surface that are occupied by one or more feature. For example, an interstitial region can separate one feature from another feature. Thus, a first metal region on a surface can be separated from a second metal region on the surface by an interstitial region. The two regions that are separated from each other can be discrete, lacking contact with each other. In another example, an interstitial region can separate a first portion of a feature from a second portion of a feature. Accordingly, two finger-like projections of a metal region can be separated by an interstitial region or an interstitial region can be the hole that separates portions of a donut-shaped metal region. As illustrated by the above examples, the separation provided by an interstitial region can be partial or full separation. An interstitial region can have a composition that is transparent to electromagnetic radiation from a particular part of the electromagnetic radiation spectrum including, for example, a part that is in the radio, microwave, infrared, visible, ultraviolet, X-ray or gamma ray parts of the spectrum.

As used herein, the term "gel" is intended to mean a semi-rigid solid that is permeable to liquids and gases. Exemplary gels include, but are not limited to those having a colloidal structure, such as agarose; polymer mesh structure, such as gelatin; or cross-linked polymer structure, such as polyacrylamide.

As used herein, the term "continuous," when used in reference to a layer that coats a surface across two or more regions, is intended to mean that the layer bridges the two or more regions. It will be understood that the layer may be composed of a material that is porous or that has structural interruptions, so long as the material forms a layer that bridges the two or more regions.

As used herein, the term "coat," when used as a verb, is intended to mean providing a layer or covering on a surface. As a result at least a portion of the surface can have a layer or cover. In some cases the entire surface can have a layer or cover. In alternative cases only a portion of the surface will have a layer or covering. The term "coat," when used to describe the relationship between a surface and a material, is intended to mean that the material is present as a layer or cover on the surface. The material can seal the surface, for example, preventing contact of liquid or gas with the surface. However, the material need not form a seal. For example, the material can be porous to liquid, gas, or one or more components carried in a liquid or gas. Exemplary materials that can coat a surface include, but are not limited to, a gel such as polyacrylamide or agarose, liquid, metal, a second surface, plastic, silica, or gas.

As used herein, reference to "selectively" manipulating a first thing compared to second thing is intended to mean that the manipulation has a greater effect on the first thing compared to the effect on the second thing. The manipulation need not have an effect on the second thing. The manipulation can have an effect on the first thing that is at least 1%, 5%, 10%, 25%, 50%, 75%, 90%, 95%, or 99% greater than the effect on the second thing. The manipulation can have an effect on the first thing that is at least 2 fold, 3 fold, 4 fold, 5 fold, 10 fold, 100 fold, $1 \times 10^3$ fold, $1 \times 10^4$ fold or $1 \times 10^6$ fold higher than the effect on the second thing. The manipulation can include, for example, modifying, contacting, treating, changing, cleaving (e.g. of a chemical bond), photo-chemically cleaving (e.g. of a chemical bond), forming (e.g. of a chemical bond), photo-chemically forming (e.g. of a chemical bond), covalently modifying, non-covalently modifying, destroying, photo-ablating, removing, synthesizing, polymerizing, photo-polymerizing, amplifying (e.g. of a nucleic acid), copying (e.g. of a nucleic acid), extending (e.g. of a nucleic acid), ligating (e.g. of a nucleic acid), or other manipulation set forth herein or otherwise known in the art.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region (or other mask region) of a surface such as those metals set forth herein. Alternatively or additionally, the part of the spectrum can be one that passes through an interstitial region of a surface such as a region made of glass, plastic, silica, or other material set forth herein. In particular embodiments, radiation can be used that is capable of passing through a metal. Alternatively or additionally, radiation can be used that is masked by glass, plastic, silica, or other material set forth herein.

The present disclosure provides a method of preparing a surface. The method can include the steps of (a) providing a surface having metal regions and interstitial regions, the interstitial regions having a composition that differs from the metal regions; (b) contacting the surface with a fluid including a polymerizable material, wherein the fluid coats the surface across the metal regions and the interstitial regions; and (c) polymerizing the polymerizable material, thereby forming a continuous gel layer that coats the surface across the metal regions and the interstitial regions, wherein portions of the gel layer that coat the metal regions have greater mass than portions of the gel layer that coat the interstitial regions.

A surface that is used in accordance with the methods set forth herein can be present on any of a variety of substrates. The surface can be located on a substrate or material that provides a solid or semi-solid foundation for a mask region or a metal region. Exemplary types of substrate materials include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, polymers and multiwell (e.g. microtiter) plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

In particular embodiments the substrate provides a support for creation of features having attached biopolymers, including nucleic acids, polypeptide and/or other polymers. Accordingly, substrates employed in the art as microarrays are particularly useful. Exemplary substrates are those used for a Sentrix® Array or Sentrix® BeadChip Array available from Illumina®, Inc. (San Diego, CA) or those described in U.S. Pat. Nos. 6,266,459; 6,355,431; 6,770,441 and 6,859,570 and PCT Publication No. WO 00/63437 (each of which is incorporated by reference in its entirety). Other arrays having useful substrates include those set forth in US Pat. Pub. Nos. 2005/0227252 A1, 2006/0023310 A1, 2006/006327 A1, 2006/0071075 A1, 2006/0119913 A1, U.S. Pat. Nos. 6,489,606; 7,106,513; 7,126,755; 7,164,533; and PCT Pub. Nos. WO 05/033681 and WO 04/024328 (each of which is hereby incorporated by reference in its entirety).

Further examples of commercially available microarrays having substrates that can be used include, for example, an Affymetrix GeneChip® microarray or other microarray such as those described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591 (each of which is hereby incorporated by reference in its entirety).

Substrates used in the manufacture of spotted microarrays can also be used. An exemplary spotted microarray is a CodeLink™ Array available from Amersham Biosciences. Another microarray made from substrates that can be useful in the invention is one that is manufactured using inkjet printing methods such as SurePrint™ Technology available from Agilent Technologies. Other substrates include, but are not limited to, those described in U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751 and PCT Pub. Nos. WO 93/17126 and WO 95/35505 (each of which is hereby incorporated by reference in its entirety).

Those skilled in the art will know or understand that the composition and geometry of a substrate can vary depending on the intended use and preferences of the user. Therefore, although planar substrates such as slides, chips or wafers are exemplified herein for illustration, given the teachings and guidance provided herein, those skilled in the art will understand that a wide variety of other substrates exemplified herein or well known in the art also can be used in the methods and/or compositions of the invention.

Generally, a surface that is used in a method or composition set forth herein will be planar. However, the surface need not be planar and can instead have surface features such as wells, pits, channels, ridges, raised regions, pegs, posts or the like. The surface can be porous or nonporous to suit particular applications. A metal region or patch can be located in or on a particular surface feature such as those set forth above. Similarly an interstitial region can be located in or on a particular surface feature. Furthermore, these or other surface features can occur within a metal region, mask region or interstitial region.

In particular embodiments, a surface or region thereof can be located in a vessel such as a well, tube, channel, cuvette, Petri plate, bottle or the like. A particularly useful vessel is a flow-cell, for example, as described in US Pat. Pub. No. 2010/0111768 A1 or Bentley et al., *Nature* 456:53-59 (2008), each of which is incorporated herein by reference in its entirety. Exemplary flow-cells are those that are commercially available from Illumina, Inc. (San Diego, CA). Another particularly useful vessel is a well in a multiwell plate or microtiter plate.

A surface can have one or more regions. The regions can be distinguished by characteristics such as composition of the region, shape of the region, size of the region, thickness of the region (e.g. in the z-dimension), location of the region on the surface (e.g. in the x or y dimension). Accordingly, two or more different regions can be distinguished based on differences in one or more characteristics.

Exemplary compositions for one or more regions include metals, such as those set forth elsewhere herein; substrate materials, such as those set forth elsewhere herein; mask materials that prevent passage of radiation in a particular range of the electromagnetic spectrum, examples of which are set forth elsewhere herein; optical filter materials that pass light in a certain wavelength range, outside of a certain wavelength range, above a certain cutoff wavelength or below a certain cutoff wavelength; non-metallic materials; or chemically reactive compositions such as those capable of attaching to a molecule of interest. In particular embodiments the reactive compositions are molecular linkers capable of covalently bonding to a molecule of interest (e.g. photo-reactive crosslinking reagents), binding agents capable of binding to another molecule via non-specific interactions (e.g. hydrogen bonding, ionic bonding, van der Waals interactions etc.) or via specific interactions (e.g. affinity interactions, receptor-ligand interactions, antibody-epitope interactions, avidin-biotin interactions, streptavidin-biotin interactions, lectin-carbohydrate interactions, etc.).

A region on a surface can have any of a variety of geometric shapes. Examples include, without limitation, rectangular, square, circular, elliptical, oval, triangular, polygonal, trapezoidal or irregular shapes. Several regions can be present on a surface in the form of an array. For example, the array of regions can appear as a grid of spots or patches. Regions that form an array can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbors or the pitch can vary between different pairs of nearest neighbors. Generally, two or more regions on a surface are separated by interstitial regions. The separation can be partial such that an interstitial region separates part of one region from part of another region. Alternatively, the separation can be sufficiently complete to render two regions discrete from each other. Thus, at least one metal region or mask region on a surface can be completely surrounded by at least a portion of an interstitial region.

The size of a region on a surface can be selected to suit a particular application. For example, in some embodiments a region can have a size that accommodates only a single nucleic acid molecule. A surface having a plurality of features in this size range is useful for constructing an array of molecules for detection at single molecule resolution. Features (e.g. metal features or mask features) in this size range are also useful for capture of a single nucleic acid template molecule to seed subsequent formation of a homogenous colony, for example, via bridge amplification. In this example, the bridge amplification can be primed by primer nucleic acids that are attached to a gel layer that is in contact with a metal feature or mask feature, the feature being attached to a single nucleic acid template. Thus, the feature can seed growth of a cluster of nucleic acid copies of the template that forms in the gel layer around the feature.

Accordingly one or more regions can each have an area that is no larger than about 25 $nm^2$, no larger than about 10 $nm^2$, no larger than about 5 $nm^2$, or no larger than about 1 $nm^2$. Larger regions are also useful, for example, to accommodate populations of nucleic acids of various sizes. Thus, one or more regions can each have an area that is no larger than about 1 mm$^2$, no larger than about 500 µm$^2$, no larger than about 100 µm$^2$, no larger than about 25 µm$^2$, no larger than about 10 µm$^2$, no larger than about 5 µm$^2$, no larger than about 1 µm$^2$, no larger than about 500 nm$^2$, or no larger than about 100 nm$^2$. Although there need not be a lower limit to the area of an individual region, in particular embodiments the region will be no smaller than about 1 mm$^2$, no smaller than about 500 µm$^2$, no smaller than about 100 µm$^2$, no smaller than about 25 µm$^2$ no smaller than about 10 µm$^2$, no smaller than about 5 µm$^2$, no smaller than about 1 µm$^2$, no smaller than about 500 nm$^2$, no smaller than about 100 nm$^2$, no smaller than about 25 nm$^2$, no smaller than about 10 nm$^2$, no smaller than about 5 nm$^2$, or no smaller than about 1 nm$^2$. Indeed, a region can have a size that is in a range between an upper and lower limit selected from those exemplified above. Although several size ranges for regions of a surface have been exemplified with respect to nucleic acids and on the scale of nucleic acids, it will be understood that regions in these size ranges can be used for applications that do not include nucleic acids. It will be further understood that the size of the regions need not be confined to a scale used for nucleic acid applications.

For embodiments that include a plurality of regions, such as an array of regions, the regions can be discrete, being separated with spaces between each other. The size of the regions and/or spacing between the regions can vary such that arrays can be high density, medium density or lower density. High density arrays are characterized as having regions separated by less than about 15 µm. Medium density arrays have regions separated by about 15 to 30 µm, while low density arrays have regions separated by greater than 30 µm. An array useful in the invention can have regions that are separated by less than 100 µm, 50 µm, 10 µm, 5 µm, 1 µm or 0.5 µm.

A metal layer can be deposited on a surface using methods known in the art such as wet plasma etching, dry plasma etching, atomic layer deposition, ion beam etching, chemical vapor deposition, vacuum sputtering or the like. Any of a variety of commercial instruments can be used as appropriate including, for example, the FlexAL®, OpAL®, Ionfab 300plus®, or Optofab 3000® systems (Oxford Instruments, UK). A metal layer can also be deposited by e-beam evaporation or sputtering as set forth in Thornton, *Ann. Rev. Mater. Sci.* 7:239-60 (1977), which is incorporated herein by reference in its entirety. Metal layer deposition techniques, such as those exemplified above, can be combined with photolithography techniques to create metal regions or patches on a surface. Exemplary methods for combining metal layer deposition techniques and photolithography techniques are provided in Example I below.

In particular embodiments, a polymerizable material is used. For example, a polymerizable material can be contacted with a surface such as a surface having metal regions, mask regions and/or interstitial regions. Typically polymerizable material is provided in a liquid state and subsequently converted to a gel, polymer or other semisolid material. Examples of polymerizable materials include, without limitation, acrylamide, methacrylamide, hydroxyethyl methacrylate, N-vinyl pyrolidinone or derivatives thereof. Such materials are useful for preparing hydrogels. In some embodiments, the polymerizable material can include two or more different species of compound that form a co-polymer. For example, two or more different species of acrylamide, methacrylamide, hydroxyethyl methacrylate, N-vinyl pyrolidinone or derivatives thereof can function as co-monomers that polymerize to form a copolymer hydrogel. Exemplary hydrogels and polymerizable materials that can be used to form hydrogels are described, for example, in US Pat. Pub. No. 2011/0059865 A1, which is incorporated herein by reference in its entirety. Other hydrogels include but are not limited to, polyacrylamide polymers formed from acrylamide and an acrylic acid or an acrylic acid containing a vinyl group as described, for example, in WO 00/31148 (incorporated herein by reference in its entirety); polyacrylamide polymers formed from monomers that form [2+2] photocycloaddition reactions, for example, as described in WO 01/01143 or WO 03/014392 (each of which is incorporated herein by reference in its entirety); or polyacrylamide copolymers described in U.S. Pat. No. 6,465,178, WO 01/62982 or WO 00/53812 (each of which is incorporated herein by reference in its entirety). Silane-free acrylamide (SFA) polymer formed by polymerization of silane free acrylamide and N—(S bromoacetamidylpentyl) acrylamide (BRAPA) is particularly useful. Methods for making and using SFA polymer are set forth in the Examples below.

Other useful polymerizable materials are those that undergo a temperature dependent change in state from liquid to gelatinous. Examples include, but are not limited to agar, agarose, or gelatin.

A polymerizable material can be contacted with a surface using techniques convenient to the material and to the surface. Typically the polymerizable material is in a liquid state and can be manipulated using known fluidics techniques. As such, liquids can be moved by hydraulic forces, pneumatic forces, displacement, pumping, gravity flow or the like. Generally, a liquid is delivered to a surface when performing a method as set forth herein. However, the surface can be brought to a liquid, for example, by dipping, immersing, floating or the like. The contacting of a liquid and a surface can be carried out by automated methods or manually. For example, an individual can manually deliver a liquid to a surface using a hand held pipette or the individual can handle a substrate to bring it into contact with a liquid. Examples of automated methods include, but are not limited to, robotic manipulations to pipette liquids to a surface or robotic manipulations to bring a substrate into contact with a liquid.

Generally, a liquid, such as a liquid containing a polymerizable material, is contacted with a surface in a way to wet the entire surface. For example, the liquid can form a continuous layer over the surface. The liquid when in a continuous layer over the surface can have uniform thickness or depth. For example, the surface can be maintained in a level orientation with respect to gravity such that the depth of the liquid over the surface is uniform. Alternatively, the depth or thickness of the liquid in the continuous layer can differ across the surface. For example, the surface can be tilted to a non-level orientation with respect to gravity such that the liquid has a greater depth over one region of the surface compared to another region of the surface. Alternatively or additionally, the surface can contain relief features that create regions of different depth.

In particular embodiments, the liquid can be in discontinuous contact with one or more regions of a surface (e.g. metal regions, interstitial regions, mask regions, or transparent regions). For example, the liquid can form droplets on the surface. The surface can contain features that retain liquids in particular regions and prevent the liquid from contacting other regions. For example the surface can include wells or channels that contain a liquid. Alternatively or additionally, the surface can have raised regions that are above the surface of a liquid and therefore not in contact with the liquid. Another way to limit contact of a liquid to only a portion of a surface is to use regions having differing hydrophilicity and hydrophobicity. An aqueous liquid can be retained in a hydrophilic region while being excluded or repelled from a hydrophobic region. Alternatively, an organic or non-polar liquid can be retained in a hydrophobic region while being excluded or repelled from a hydrophilic region. Thus, regions set forth herein with respect to particular characteristics can have a further characteristic of being hydrophobic or hydrophilic.

In embodiments utilizing a flow-cell, a polymerizable material can be delivered to the flow-cell in a volume that fills the flow-cell partially or fully. Thus, the flow-cell can contain no gas bubbles (e.g. when fully filled), or it can contain one or more gas bubbles (e.g. when partially filled).

A polymerizable material can be kept in a liquid state during one or more manipulation or step in a method set forth herein. For example, a chemically polymerizable material can be kept separated from a second material or chemical that causes polymerization to form a gel. In a further example, a photo-polymerizable material can be maintained in a dark environment or at least in an environment that is masked, filtered or otherwise blocked from light having a wavelength that induces the photo-polymerization. The material can also be maintained at a temperature that prevents or inhibits polymerization. For example, agarose can be maintained at a temperature that is above its melting temperature or hydrogel precursors can be kept at a temperature that prevents or inhibits polymerization.

A polymerizable material, once present at a desired location, such as on a surface, can be polymerized using a method appropriate to the material to form a gel. The appropriate method will be known to those skilled in the art in view of the known or determinable properties and characteristics of the material. For example, a hydrogel can be polymerized using methods set forth in US Pat. Pub. No. 2011/0059865 A1, WO 00/31148, WO 01/01143, WO 03/014392, U.S. Pat. No. 6,465,178, WO 01/62982 or WO 00/53812, each of which is incorporated herein by reference in its entirety. Agar, agarose, gelatin and other materials that undergo a temperature dependent solidification can be polymerized by reducing the temperature of the material to form a gel.

In many embodiments, a gel made or used in a method set forth herein will be a continuous gel layer with respect to coverage of a surface. The gel can thus form a layer that is uninterrupted across several regions of a surface including, for example, two or more metal regions or interstitial regions on a metal patterned surface. The gel when in a continuous layer over a surface can have uniform thickness or depth. Alternatively, the depth or thickness of the gel in the continuous layer can differ across the surface. As such the gel is understood to be continuous with respect to spanning across several regions of a surface even if the thickness of the gel differs over two or more regions of the surface, so long as the thickness is greater than zero. An example of a system where a gel can be continuous and yet have different thickness over different regions is when a gel covers a surface that contains relief features. Here the relief features create regions of different depth, much like the difference in ocean depth over trenches and reefs that form relief features on the ocean floor. Alternatively or additionally, the gel can have a greater depth over a region at or near a first end of the surface compared to the depth at a region at or near the other end of the surface. Such a difference in depth would occur for example if the gel formed while the first end of the surface was held at a lower position with respect to gravity (compared to the position of the second end).

In particular embodiments, a gel can be discontinuous with respect to its coverage of two or more regions of a surface. More specifically, two or more regions of gel can be separated by a region where there is no gel. For example, the gel can form two or more discrete features on the surface. The features can form patches of gel with a surface contact area (i.e. a footprint) having shapes, sizes or pitch similar to those set forth herein with regard to metal patches. Indeed, in some embodiments the gel patch can coat a metal region or interstitial region such that the footprint of the gel patch has perimeter boundaries defined by the shape and size of the metal region or interstitial region, respectively. Such gel features can be formed, for example, by the use of near-field masks and photo-polymerization as set forth in Examples II and III, below. Patches or regions of gel at two or more discontinuous regions can have the same or different thickness.

The depth of a gel layer, or portion thereof, can differ for particular applications of the methods set forth herein. The depth can be, for example, in the nanometer, micron or millimeter range or higher if desired. In particular embodiments, a gel layer can have a depth that is at least about 10 nm, 25 nm, 50 nm, 100 nm, 500 nm, 1 µm, 10 µm, 50 µm, 100 µm, 500 µm, 1 mm, 10 mm, 100 mm or higher. Alternatively or additionally, the depth of a gel layer can be at most about 100 mm, 10 mm, 1 mm, 500 µm, 100 µm, 50 µm, 10 µm, 1 µm, 500 nm, 100 nm, 50 nm, 25 nm, 10 nm or 1 nm. It will be understood that a gel layer made or used in a method set forth herein can have a depth that ranges between two of the exemplary boundaries set forth above. It will also be understood that the ranges are merely exemplary and are not intended to limit all embodiments of the invention; rather a gel layer can have a depth that extends beyond the lower or upper boundaries exemplified above.

A gel, whether continuous or discontinuous, can have non-uniform thickness across different regions of a surface. For example, in embodiments set forth herein, portions of a gel layer that coat metal regions can be thicker than portions of the gel layer that coat interstitial regions. Such a configuration can result for example, due to metal-enhanced polymerization of SFA. Thus, a metal patterned surface can have gel regions of greater mass over metal patches compared to the mass of the gel regions over interstitial regions. The greater mass can be manifested as one or more of increased thickness, increased density or increased volume of gel. Exemplary methods believed to form greater gel mass over metal regions compared to interstitial regions are provided in Example I. Alternatively, portions of a gel layer that coat metal regions can have lower mass than portions of the gel layer that coat interstitial regions. Examples II and III set forth embodiments wherein a lower mass of gel is believed to form over metal regions compared to the thickness of the gel formed over interstitial regions. The difference in gel mass can correlate with different properties of a surface, such as presence or absence of a metal coating as demonstrated in the Examples, however gel mass can also differ for regions of a surface that are the same. For example, gel thickness, density or volume can be non-uniform across a metal coating on a surface.

For embodiments where a gel has different mass (e.g. depth, thickness, volume or density) at different locations on a surface, the difference can range from a difference of a few percentage points to a difference of several fold. For example, the gel present at a first region of a surface can have at least about 10%, 25%, 50%, 75% or 100% more mass than the gel present at a second comparably sized region of the surface. Larger differences in mass of at least about 2 fold, 3 fold, 4 fold, 5 fold, 10 fold, 25 fold 50 fold, 100 fold or more are also useful. Alternatively or additionally, the difference in mass for gel over different, comparably sized regions of a surface can have an upper limit that is at most about 100 fold, 50 fold, 25 fold, 10 fold, 5 fold, 4 fold, 3 fold, 2 fold, 100%, 75%, 50%, 25%, 10% or lower. For example, the difference in mass for a gel over a surface, in many embodiments, can be negligible, or indistinguishable to effectively approach a state where the mass of the gel is uniform across a gel layer whether the layer is continuous or discontinuous over a surface.

A gel can have uniform or non-uniform density across different regions of a surface. For example, in embodiments set forth herein, portions of a gel layer that coat metal regions can have higher density than portions of the gel layer that coat interstitial regions. Higher density can be characterized, in some embodiments, as a decreased porosity for the gel or as an increase in the number of cross links per volume of the gel. Higher density gel can result for example, due to metal induced polymerization of SFA. Thus, a metal patterned surface can have higher density gel regions over metal patches compared to the density of the gel regions over interstitial regions. Example I provides methods believed to form a higher density gel layer over metal regions compared to the density of the gel formed over interstitial regions. Alternatively, portions of a gel layer that coat metal regions can be less dense than portions of the gel layer that coat interstitial regions. Examples II and III set forth embodiments wherein a lower density gel layer is believed to form over metal regions compared to over interstitial regions. The difference in gel density can correlate with different properties of a surface, such as presence or absence of a metal coating as demonstrated in the Examples, however gel density can also differ for regions of a surface that are the same. For example, gel density can be non-uniform across a metal coating on a surface.

The formation of a gel layer in the methods set forth herein is exemplary of other molecular layers that can be formed using similar methods. Accordingly, the methods set forth herein can be used to produce any of a variety of molecular layers including those that may not be characterized as gels such as polymer brush surfaces, nanofilament surfaces, etc. Furthermore an array of the present disclosure can include a continuous molecular layer in place of the continuous gel layers exemplified herein. In particular embodiments, a method of making a nucleic acid array is provided. The method can include the steps of (a) providing a surface having metal regions and interstitial regions, the interstitial regions having a composition that differs from the metal regions, wherein a continuous gel layer coats the surface across the metal regions and the interstitial regions; and (b) contacting the continuous gel layer with a fluid including nucleic acids under conditions wherein the nucleic acids become attached to the gel layer and wherein a greater amount of the nucleic acids from the fluid attach to portions of the gel layer that coat the metal regions than the amount of nucleic acids that attach to portions of the gel layer that coat the interstitial regions.

A method set forth herein, can include a step of attaching a nucleic acid to a gel layer. This can be achieved, for example, by contacting the gel with a fluid containing the nucleic acids under conditions wherein the nucleic acids attach to the gel. The contacting of the nucleic acid and gel can occur under conditions wherein a uniform concentration of the nucleic acids contacts the portions of a continuous gel layer that coat different regions of the surface, such as metal regions and interstitial regions. A liquid that contains nucleic acids can be delivered using methods set forth above in regard to delivery of liquids bearing polymerizable materials.

Generally covalent attachment of the nucleic acids to the gel is desired. However, non-covalent attachment can also be useful. Methods for attaching nucleic acids to gels are known in the art and include, for example, one or more of those described in US Pat. Pub. No. 2011/0059865 A1, WO 2007/135368, or WO 2008/093098, each of which is incorporated herein by reference in its entirety. The nucleic acids can be attached to the gel via their 3' oxygen, 5' oxygen, or at other locations along their length such as via a base moiety of the 3' terminal nucleotide, a base moiety of the 5' nucleotide, and/or one or more base moieties elsewhere in the molecule. Non-covalent modes of attachment include, for example, ionic interactions between nucleic acid and gel, entrapment of nucleic acid within pores of a gel, binding between receptors and ligands on the gel and/or nucleic acid, and other known modes.

Nucleic acids that are made or used in methods set forth herein can be DNA or RNA or derivatives thereof such as peptide nucleic acids. Exemplary derivatives of nucleic acids and nucleotides that are useful in the methods and compositions set forth herein are described, for example, in U.S. Pat. No. 7,582,420; 6,890,741; 6,913,884 or 6,355,431, each of which is incorporated herein by reference in its entirety. In particular embodiments a population of nucleic acids having the same sequence is attached to a gel. Thus, the gel can have a single species of attached nucleic acids. Alternatively, a population of nucleic acids having different sequences can be attached to a gel. For example, a population of 2 primer types, useful for amplification of a sequence flanked by priming sites that complement the 2 primer types, can be attached to a gel. In particular embodiments, different nucleic acids, such as one or more different primer types (i.e. having one or more different sequences) can be distributed randomly throughout the gel. For example, a solution of different nucleic acids can be contacted with the gel such that the nucleic acids diffuse to random locations where they can attach. Alternatively, the different nucleic acids can be located at predefined or known locations, for example using array techniques.

Exemplary array techniques that are useful include, without limitation, those used in making a Sentrix® Array or Sentrix® BeadChip Array available from Illumina, Inc. (San Diego, CA) or others including beads such as those described previously herein. Further array techniques are those used in the commercial manufacture of arrays from Affymetrix such as the GeneChip® microarrays or other microarray synthesized in accordance with techniques sometimes referred to as VLSIPS™ (Very Large Scale Immobilized Polymer Synthesis) technologies as described, for example, previously herein. Spotting techniques can also be used such as those used for manufacture of a CodeLink™ Array available from Amersham Biosciences. Printing methods are also useful such as those used for SurePrint™ arrays available from Agilent Technologies.

Accordingly, this disclosure provides a method of making a nucleic acid array. In particular embodiments, the method includes the steps of (a) providing a surface having metal regions and interstitial regions, the interstitial regions having a composition that differs from the metal regions, wherein a continuous gel layer coats the surface across the metal regions and the interstitial regions; (b) contacting the continuous gel layer with a fluid comprising nucleic acids; and (c) selectively modifying the portions of the gel layer that coat the interstitial regions compared to the portions of the gel layer that coat the metal regions, thereby attaching the nucleic acids to the gel layer, wherein a greater amount of the nucleic acids from the fluid attach to portions of the gel layer that coat the metal regions than the amount of nucleic acids that attach to portions of the gel layer that coat the interstitial regions.

Nucleic acids that are attached to a gel, for example in the format of an array but also in other formats, can be used for any of a variety of purposes. A particularly desirable use for the nucleic acids is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. No. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety. For example, a label can be recruited to a capture probe by virtue of hybridization of the capture probe to a target probe that bears the label. In another example, a label can be recruited to a capture probe by hybridizing a target probe to the capture probe such that the capture probe can be extended by ligation to a labeled oligonucleotide (e.g. via ligase activity) or by addition of a labeled nucleotide (e.g. via polymerase activity).

A further use for nucleic acids that are attached to a gel is for priming amplification of a template nucleic acid. In an exemplary method, the template nucleic acid hybridizes to a gel-attached primer and the 3' end of the primer is extended to create a complementary copy of the template. In some embodiments two different primers can be attached to the gel. The primers can form a pair used for amplification of a template and its complementary copy. As such, two primers can be used for amplification of the template into multiple copies to form a cluster or population of amplicons. For example, amplification can be carried out using bridge amplification to form nucleic acid clusters attached to the gel. Useful bridge amplification methods are described, for example, in U.S. Pat. Nos. 5,641,658 and 7,115,400; U.S. Pat. Pub. Nos. 2002/0055100 A1, 2004/0096853 A1, 2004/0002090 A1, 2007/0128624 A1, and 2008/0009420 A1, each of which is incorporated herein by reference in its entirety. Another useful method for amplifying nucleic acids using a gel-attached primer is rolling circle amplification (RCA). RCA can be carried out, for example, as described in Lizardi et al., Nat. Genet. 19:225-232 (1998) and US Pat. Pub. No. 2007/0099208 A1, each of which is incorporated herein by reference in its entirety. The primers can also be used in a multiple displacement amplification (MDA) reaction, for example, using a product of RCA (i.e. an RCA amplicon) as a template. Exemplary methods of MDA are described in U.S. Pat. Nos. 6,124,120; 5,871,921; and EP 0,868,530 B 1, each of which is incorporated herein by reference in its entirety.

A surface having a metal region and interstitial region can further include one or more nucleic acids over the metal region. Additionally, one or more nucleic acids can optionally be present over the interstitial region. As set forth above, the nucleic acids over these regions are typically attached to a gel. However, a gel is optional and need not be present for all embodiments of the invention. In some embodiments the amount or concentration of nucleic acid molecules over the metal region will exceed the amount or concentration of nucleic acids over the interstitial region. For example, the amount or concentration of nucleic acids over the metal region can be at least about 10%, 25%, 50%, 75% or 100% more than the amount or concentration of nucleic acids present over a comparably sized area of the interstitial region. Larger differences in amount or concentration of at least about 2 fold, 3 fold, 4 fold, 5 fold, 10 fold, 25 fold 50 fold, 100 fold or more are also possible. Alternatively or additionally, the difference in the amount or concentration of nucleic acids over the metal region in comparison to a comparable sized area of the interstitial region can have an upper limit that is at most about 100 fold, 50 fold, 25 fold, 10 fold, 5 fold, 4 fold, 3 fold, 2 fold, 100%, 75%, 50%, 25%, 10% or lower. The amount or concentration of nucleic acids present over a metal region can be between two or more of the exemplary boundaries above. Similar boundaries and ranges can occur for the amount or concentration of nucleic acids present over other mask regions as well. In particular embodiments, the amount or concentration of nucleic acids over the interstitial regions is substantially none.

The amount or concentration of nucleic acid molecules over a metal region can exceed the amount or concentration of nucleic acids over an interstitial region in embodiments wherein the metal region produces increased density of gel or produces increased grafting of primers to the gel. The methods set forth in Example I can be used for production of a patterned surface wherein a greater amount or concentration of nucleic acid molecules is present over metal regions compared to interstitial regions. Selective photolysis or laser ablation of nucleic acids over interstitial regions, while masking nucleic acids over metal regions can also be used. An exemplary method utilizing masking and laser ablation is described in Example II. Mask regions having non-metallic materials can be used similarly.

In an alternative method, masking can be used to selectively prevent or reduce attachment of nucleic acids over metal regions (or regions of other mask material) compared to over interstitial regions. Again the nucleic acids over the two types of regions can optionally be attached to a gel layer. In one example, a photo-chemically activated cross-linking agent can be used to selectively polymerize a polymerizable material to form a gel over an interstitial region, whereas polymerizable material over a metal region is masked from photo-chemical activation such that little to no gel forms over the metal region. An exemplary technique is set forth in Example III. Similarly, a photo-chemically active agent can be used to graft a nucleic acid to a gel such that irradiation with the proper wavelength results in grafting of the nucleic acid to a gel or to the surface over the interstitial region, whereas little to no nucleic acid is grafted to the gel or surface over the metal region.

Figure 10:
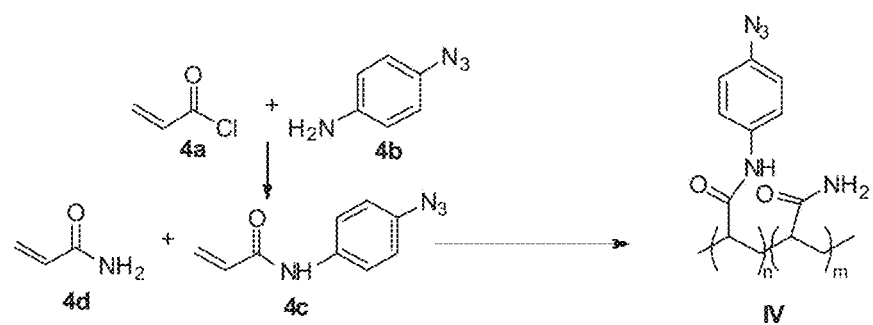
FIG. 10 shows a synthetic scheme for a photo-polymerizable material.

A further exemplary method for selectively photo-polymerizing material to form a gel over an interstitial region is shown in FIG. 10 and further described in the provisional application U.S. Ser. No. 61/657,508. As shown in the figure, acrylamide and a new monomer 4c (synthesized via a simple one-step procedure), can be polymerized using free-radical polymerization analogous to the preparation of polyacrylamide.

Accordingly, the amount or concentration of nucleic acid molecules over an interstitial region can exceed the amount or concentration of nucleic acids over a comparably sized area of a metal region or other mask region. For example, the amount or concentration of nucleic acids over the interstitial region can be at least about 10%, 25%, 50%, 75% or 100% more than the amount or concentration of nucleic acids present over the metal region or other mask region. Larger differences in amount or concentration of at least about 2 fold, 3 fold, 4 fold, 5 fold, 10 fold, 25 fold 50 fold, 100 fold or more are also possible. Alternatively or additionally, the difference in the amount or concentration of nucleic acids over the interstitial region in comparison to a comparably sized area of a metal region (or mask region) can have an upper limit that is at most about 100 fold, 50 fold, 25 fold, 10 fold, 5 fold, 4 fold, 3 fold, 2 fold, 100%, 75%, 50%, 25%, 10% or lower. The amount or concentration of nucleic acids present over an interstitial region can be between two or more of the exemplary boundaries above. In particular embodiments, the amount or concentration of nucleic acids over the metal regions is substantially none.

Although methods for making and using surfaces are exemplified herein with respect to nucleic acids, it will be understood that other analytes can be attached to a gel. Exemplary analytes include, without limitation, nucleotides, amino acids, proteins, peptides, antibodies, lectins, sugars, polysaccharides, metabolites, candidate compounds of a synthetic library and analogs thereof. Known methods can be used to synthesize, attach and detect any of a variety of analytes used in a method set forth herein.

A metal region can optionally be removed from a surface. For example, a metal coating can be removed from a surface by physical or chemical means. Exemplary physical means include, but are not limited to, polishing, sanding, lapping or grinding the surface to remove the metal coat with abrasive forces; heating the surface to thermally melt or degrade the metal; peeling the metal coating from the surface; laser ablating the metal from the surface, or the like. Exemplary chemical means include, without limitation, treatment with acid, base (i.e. alkaline treatment), caustic solvents, $Al_2O_3$ hydrolysis, or the like. Specific examples of useful etchants include, without limitation persulfate, sulfuric acid, chromic-sulfuric acid, orthophosphoric acid and derivatives thereof such as TRANSETCH-N (Transene Company Inc., Danvers MA), cupric chloride with the copper complexed with ammonia, and etchants described in Williams et al., *J. Micromelectromechanical Sys.* 12:761-778 (2003) (incorporated herein by reference in its entirety) such as isotropic silicon etchant, potassium hydroxide (KOH), hydrofluoric acid (HF), buffered hydrofluoric acid (BHF), hot phosphoric acid, titanium wet etchant, chromium etchant, molybdenum etchant, warm hydrogen peroxide, copper etchants, hot sulfuric and phosphoric acids, acetone, methanol, isopropanol, xenon difluoride, HF and $H_2O$ vapor, and oxygen plasma. A combination of physical and chemical means can be used to remove a metal coating from a surface.

Removal of a metal region from a surface can be carried out at different points in the processing of a substrate in accordance with a desired use for the substrate. For example, a metal coating can be removed before or after a gel is formed on the surface that is coated by the metal. In the latter case, the metal coating can be removed using conditions that preserve the gel layer on the surface. In particular embodiments, the metal coating can be removed after formation of the gel and after grafting of nucleic acids to the gel. Furthermore, if desired the metal coating can be removed after formation of the gel, after grafting of nucleic acids to the gel and after the nucleic acids are used in a process such as hybridization to other nucleic acids, bridge amplification, detection of labels present at the nucleic acids or at amplicons produced from the nucleic acids, or a combination of these or similar steps carried out on the nucleic acids grafted to the gel. As set forth in Example I, metal can be removed from a surface before, after or during removal of a photo-resist material from the surface.

A variety of manipulations that can be carried out during the manufacture and use of a surface are set forth in further detail herein, or known in the art, one or more of which can be carried out prior to removal of a metal from the surface. Thus, the metal regions can be removed from the surface under conditions wherein the nucleic acids remain attached to the gel layer on the surface. Alternatively, a metal region can be removed from a surface prior to carrying out one or more of the manipulations or steps set forth above or elsewhere herein.

Retaining a metal coating on a surface can provide advantages for making and using the surface. For example, a metal region can provide a near-field mask to protect regions of a liquid, gel or chemical components attached to the gel (such as nucleic acids, proteins, and other analytes of interest) from radiation. This protection can block substances located opposite the mask (the orientation being with respect to impinging radiation) from the effects of photolysis, photo-cleavage, photo-ablation, photo-chemical modification and other photo-chemical processes. For embodiments that use a metal patterned surface, regions of a liquid, gel or chemical components attached to the gel that coat or are otherwise present at non-metal containing, interstitial regions will not be masked from the radiation and can therefore experience the effects of photo-chemical processes. Examples II and III set forth methods where metal regions are used as near-field masks. Retaining a metal coating can also provide advantages for the detection of analytes. For example, the metal surface can serve to reflect optical signals to achieve signal amplification during fluorescence detection methods or other optical detection methods. Other advantages will be apparent to those skilled in the art in view of the characteristics of the metal coated surface as set forth herein and further in view of the desired use of the surface.

The use of near-field masks on surfaces and photo-induced manipulations of materials on the surfaces is often exemplified herein with respect to metal regions, glass or silica interstitial regions and radiation having wavelengths in the UV-VIS-IR parts of the radiation spectrum. However, it will be understood that the methods are also applicable to other mask materials, interstitial region materials and radiation wavelengths.

Accordingly methods are provided for preparing a surface, including the steps of (a) providing a surface having mask regions and transparent regions, the mask regions having a composition that blocks transmittance of radiation in a first part of the electromagnetic radiation spectrum and transparent regions having a composition that transmits radiation in the first part of the electromagnetic radiation spectrum; (b) contacting the surface with a fluid comprising a photo-polymerizable material, wherein the fluid coats the surface across the mask regions and the transparent regions; and (c) selectively photo-polymerizing the portions of the fluid that coat the transparent regions over the portions of the fluid that coat the mask regions, thereby forming a gel that coats the transparent regions.

Also provided is a method of making a nucleic acid array. The method can include the steps of (a) providing a surface having mask regions and transparent regions, the mask regions having a composition that blocks transmittance of radiation in a first part of the electromagnetic spectrum and transparent regions having a composition that transmits radiation in the first part of the electromagnetic radiation spectrum, wherein a continuous gel layer coats the surface across the mask regions and the transparent regions; (b) contacting the continuous gel layer with a fluid including nucleic acids under conditions wherein the nucleic acids become attached to the gel layer and wherein a first subpopulation of the nucleic acids attach to portions of the gel layer that coat the mask regions and a second subpopulation of nucleic acids attach to portions of the gel layer that coat the transparent regions; and (c) irradiating the surface with radiation in the first part of the electromagnetic spectrum, thereby selectively modifying the nucleic acids of one of the subpopulations compared to the nucleic acids of the other subpopulation.

As set forth previously herein, a mask region can be made from one or more metal materials. Other materials are also useful when used to mask radiation of an appropriate wavelength. For example, glass can serve as a mask for radiation in the far UV. Glass can be doped with dyes or other materials that are opaque to radiation in a particular wavelength. Band gap semiconductors are also useful. Exemplary materials that can be used for a mask include, but are not limited to those, used in commercial optical filters available from suppliers such as Edmund Optics (Barrington NJ), Chroma (Bellows Falls, VT), and Omega Optical (Brattleboro, VT). The use of such materials can provide masking in desired wavelength ranges, including for example, in one or more of the UV, VIS, or IR parts of the radiation spectrum. The mask can provide a cutoff such that radiation below a certain wavelength is blocked or such that radiation above a certain wavelength is blocked. In certain embodiments the mask can act as a bandpass filter to pass wavelengths within a particular range while blocking wavelengths outside of this range. Alternatively, the mask can act as a bandstop filter to block wavelengths within a particular range while passing wavelengths outside of this range.

Radiation used in a method set forth herein can be derived from any of a variety of sources that is appropriate for generation of radiation in a desired wavelength range. Exemplary sources include a lamp such as an arc lamp or quartz halogen lamp; light emitting diode (LED); or laser, such as a solid state laser, dye laser, photonic crystal laser, semiconductor laser or gas laser. Accordingly, the radiation can be collimated as produced by a laser or non-collimated as produced from a lamp. The radiation can be directed to a surface such that it impinges on the side of a mask that is opposite the side where a material to be protected resides. For example, radiation can be directed to the underside of a flow-cell or other substrate, such that it hits the underside of a mask whereby a liquid, gel or nucleic acid present over the mask (e.g. as a coating) is protected from the radiation. Any liquid, gel or nucleic acid present at a location over a transparent region of the flow-cell or substrate will be contacted with the radiation in this configuration.

Radiation that passes through a surface can selectively modify a material coating the surface, or otherwise present over the surface, in any of a variety of ways. As set forth above, the modification can be selective with respect to being greater for material above a transparent region of the surface as compared to material above a mask region. For example, material above the mask region can be substantially unmodified while material above the transparent region is modified. The degree of modification can be controlled for example by duration of irradiation, intensity of radiation or a combination thereof. As such the amount of a material above a mask region of a surface that is modified can be less than about 50%, less than about 25%, less than about 10%, less than about 5% or less than about 1% of the amount that is modified above a comparably sized area of a transparent region of the surface.

Any of a variety of the materials set forth herein as coating or otherwise being present over a transparent region of a surface can be modified by radiation in a method or composition set forth herein. For example, a polymerizable material can be modified to form a gel layer via photo-activation of a photo-reactive crosslinking group. In another example, a gel material can be heated, ablated, photolysed, or modified by attachment of a moiety from a photo-reactive reagent. Exemplary photo-reactive reagents are photo-crosslinkers that form a linker between a gel and another moiety (e.g. a moiety can be a surface or nucleic acid) when irradiated by the appropriate wavelength of light. Other photo-reactive reagents are photo-reactive moieties that are present on a gel or on a moiety that is to be attached to a gel. In this case irradiation with the appropriate wavelength of light will cause a linkage between the gel and the moiety. Photo-reactive reagents are known in the art and can be obtained from commercial sources such as Invitrogen (a subsidiary of Life Technologies, Carlsbad, CA), Glenn Research (Sterling, VA), Thermo Scientific (Rockford, IL) or Sigma-Aldrich (St. Louis, MO). Exemplary moieties that can be attached to a gel by photo-reaction are a nucleic acid, protein, antibody, metabolite, polysaccharide, nucleotide, amino acid or other analyte of interest, such as those set forth elsewhere herein.

Analytes, such as nucleic acids, can be modified in other ways by radiation as well. For example the photo-reactive reagents set forth above can be used to attach the nucleic acids to the surface of a substrate, to attach two or more nucleic acids to each other, or to attach another analyte to the nucleic acid. Other radiation mediated modifications of nucleic acids include photolysis, ablation, removal, or bleaching to destroy an optical label present on the nucleic acid. For example, a nucleic acid can be attached to a gel or surface via a photo-cleavable linker such that irradiation releases the nucleic acid. The nucleic acid can then be washed away. A particularly useful photo-reaction is crosslinking of nucleic acids strands using psoralen irradiated with UV light.

In some embodiments a flow-cell or other vessel having multiple surfaces is used. Vessels having multiple surfaces can be used such that only a single surface is treated using methods set forth herein. Alternatively two or more surfaces present in the vessel can be treated. For example, opposing surfaces in the interior of a flow cell can be selectively addressed with focused radiation using methods known in the art such as confocal techniques. Useful confocal techniques and devices for selectively directing radiation to multiple surfaces of a vessel (e.g. a flow cell) are described, for example, in US 2009/0272914 A1, which is incorporated herein by reference in its entirety.

Alternatively or additionally to the use of focusing techniques, different surfaces of a vessel, such as opposing interior surfaces of a flow cell, can be selectively addressed by masking with a masking liquid or masking gel. For example, a liquid that is opaque to UV radiation can be introduced into a flow cell prior to treating a first interior surface (e.g. the bottom interior surface) of the flow cell with UV light. At least portions of the first interior surface of the flow cell can be transparent to the UV light such that the portions will be altered by the UV light, for example, to photo-cleave a gel or analyte, or to photo-activate a gel or analyte in accordance with techniques set forth herein. However, UV light will be prevented from contacting the opposing interior surface (e.g. the top interior surface) of the flow cell since the UV light will be masked by the liquid that is present in the flow cell. The use of a masking liquid or masking gel that is opaque to radiation of a particular wavelength is particularly useful when two or more surfaces are otherwise susceptible to radiation at that wavelength (e.g. the surfaces may both be modified by the radiation or detected due to the radiation). The masking liquid or masking gel can be used to selectively mask at least one surface (e.g. a surface that is oriented opposite a target surface with respect to the direction from which radiation impinges). An advantage of using a liquid mask or gel mask in this way is that the mask can optionally be removed from the vessel such that the vessel can be used for subsequent manipulations where masking between surfaces is not desired. Of course in some embodiments, the masking liquid or masking gel need not be removed, for example, if it does not have properties of blocking radiation of a second wavelength that is subsequently used with the vessel.

Those skilled in the art will know or be able to determine an appropriate masking liquid or masking gel to use based on the guidance set forth herein, the desired wavelength of radiation to be masked, and known optical properties of masking liquids or gels. For example, radiation in the UV range can be masked using benzophenone, titanium dioxide or carbon black. The wavelength regions that can be masked or blocked include, without limitation, those set forth herein with regard to other embodiments. Furthermore, the concentration of masking or absorbing species in a liquid or gel can be selected to influence the depth of penetration for a particular wavelength of radiation into the liquid. The depth of penetration can be readily predicted using Beer's Law and known optical properties of the masking or absorbing species. Thus, a masking liquid or masking gel can allow treatment of a material that is on a vessel or in a vessel at a particular distance from a surface, while masking material that is on the vessel or in the vessel at a location beyond the particular distance.

Furthermore, in the case of embodiments set forth herein that use surfaces covered with a gel layer, a masking liquid or masking gel can be used that does not penetrate the gel layer. In such an embodiment, radiation can pass into a vessel through an exterior surface to which the gel layer is attached and treatment or detection of the gel layer (or contents therein) can be achieved. In this scenario, a masking liquid or masking gel that is present outside of the gel layer can prevent the radiation from impinging the volume of the vessel (or other surfaces of the vessel) that are outside of the gel layer. Alternatively, if desired a masking liquid or masking gel can be used that penetrates a gel layer, thereby masking all or part of the gel layer from radiation of a particular wavelength.

This disclosure further provides a method for preparing a surface that includes the steps of (a) providing a surface having mask regions and transparent regions, the mask regions having a composition that blocks transmittance of radiation in a first part of the electromagnetic radiation spectrum and transparent regions having a composition that transmits radiation in the first part of the electromagnetic radiation spectrum, the surface further including photo-reactive crosslinking reagents attached thereto; (b) contacting the surface with a fluid comprising a photo-polymerizable material, wherein the fluid coats the surface across the mask regions and the transparent regions; and (c) selectively irradiating the portions of the fluid that coat the transparent regions compared to the portions of the fluid that coat the mask regions, wherein the portions of the fluid that coat the transparent regions are photo-polymerized to form a gel and wherein the gel is photo-crosslinked to the surface at the transparent regions.

As exemplified by the above method, a material that is present over a transparent region of a surface (e.g. in a fluid form or gel form) can be modified by radiation in a method or composition set forth herein. For example, a polymerizable material can be modified to form a gel layer via photo-activation of a photo-reactive crosslinking group and/or the material can be photo-crosslinked to the surface.

In some embodiments, the photo-reactive crosslinking reagents include optionally substituted phenyl azide groups. In some of these embodiments, the phenyl azide is prepared by reacting an amino group with N-hydroxysulfosuccinimidyl-4-azidobenzoate (sulfo-HSAB). In some embodiments, the phenyl azide is photo-activated prior to polymerizing the polymerizable material on the surface of the substrate. In a preferred embodiment of such methods, the photo-activated functional groups generate nitrene. In another preferred embodiment of such methods, the polymer coating is covalently bonded to nitrene via photo-activation.

Figure 8:
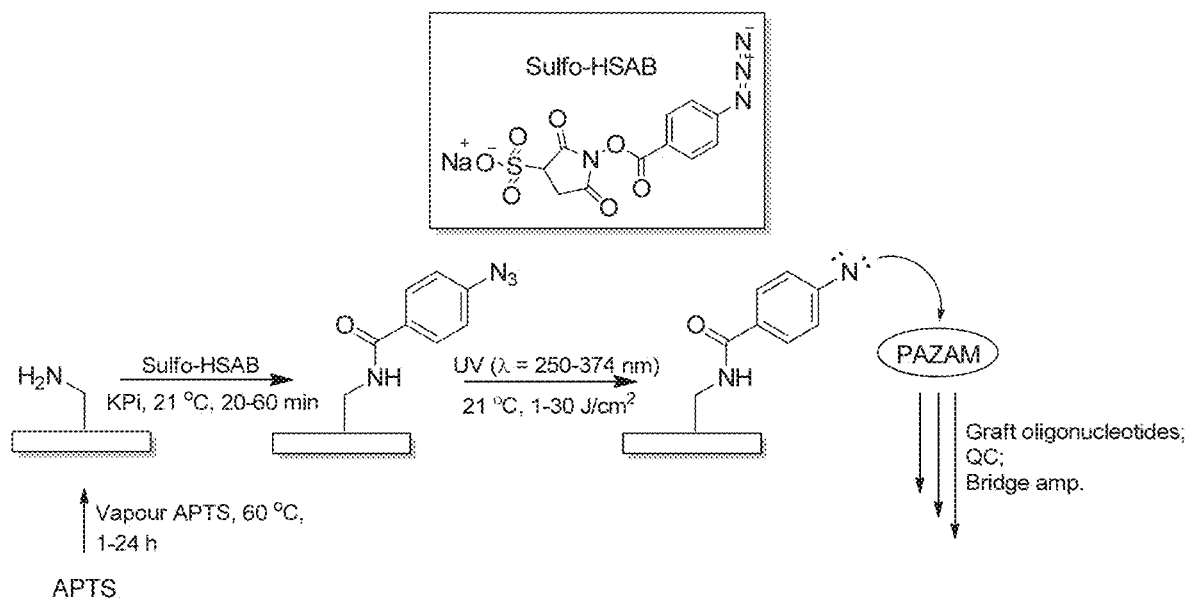
FIG. 8 shows a synthetic scheme for attaching a photo-reactive crosslinking reagent to a surface and photo-crosslinking a gel to the surface.

Sulfo-HSAB is a commercially available bifunctional crosslinking agent having a photoactive aryl azide and an activated NHS unit. Upon exposure to UV light (~254-365 nm), the aryl azide generates a nitrene with the release of nitrogen. This highly reactive species can undergo a variety of rapid insertion reactions. A pathway to prepare a photo-active surface is shown in FIG. 8 and further described in the provisional application U.S. Ser. No. 61/657,508. Briefly, a surface is pre-treated with APTS (methoxy or ethoxy silane) and baked to form an amine monolayer. The amine groups are then reacted with sulfo-HSAB to form an azido derivative. UV activation then generates the active nitrene species, which can readily undergo a variety of insertion reactions with poly(N-(5-azidoacetamidylpentyl) acrylamide-co-acrylamide) (PAZAM).

Figure 9:
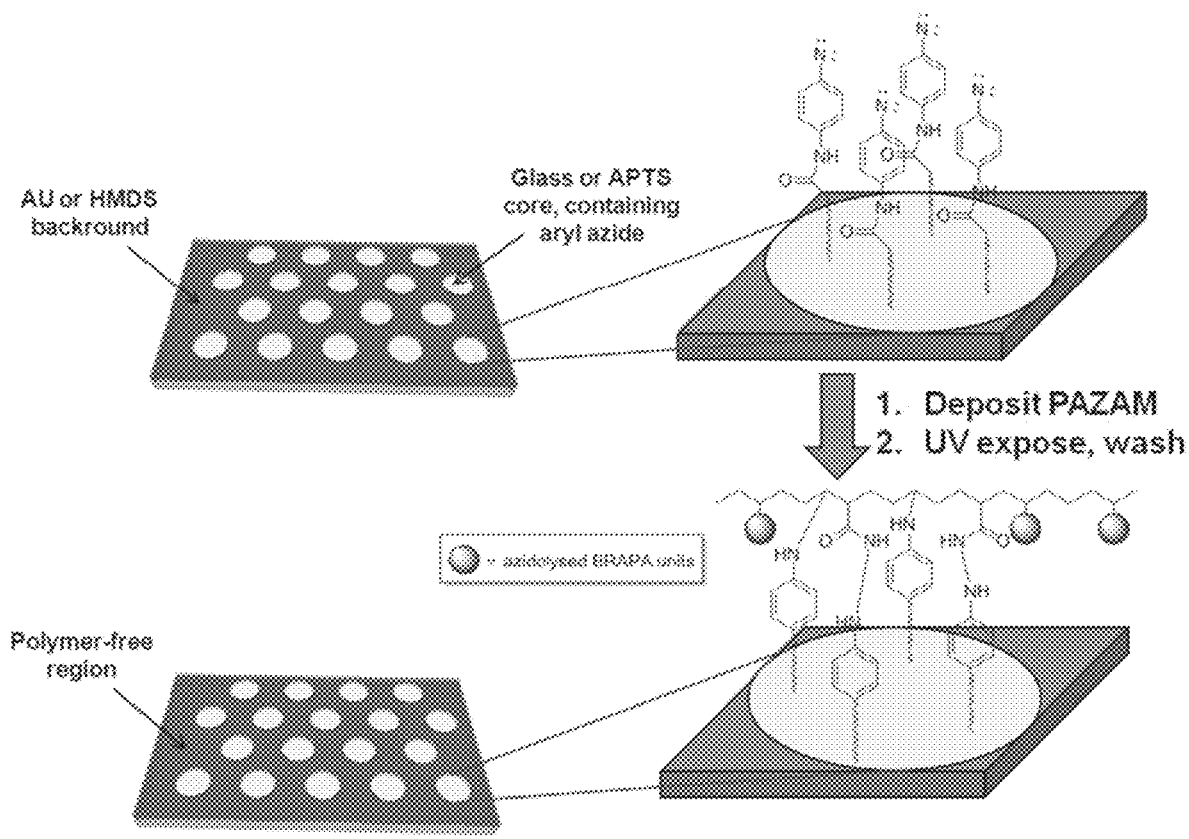
FIG. 9 shows a surface having a photo-reactive crosslinking reagent at transparent regions patterned on a surface and a photoreaction to crosslink a gel to the surface at the transparent regions.

A photo-reactive crosslinking reagent, like the azido derivative of sulfo-HSAB, can be located on a surface and photo-crosslinked to a polymer like PAZAM using UV exposure at transparent areas of a surface. The surface can have both mask regions and interstitial regions such that the polymer is selectively linked to interstitial regions and not to mask regions. An exemplary process is demonstrated in FIG. 9. As shown, the mask region is left free of any coupled polymer because the photo-reactive crosslinker is activated only (and in some cases initially located only) at the transparent patch. The radical insertion reaction is confined to a monolayer at the surface minimizing the uncontrolled propagation of radicals. Aryl azides functionalized with silane and phosphate units can also be readily accessed from commercially available starting materials, allowing anchoring to a wide variety of patch types. Further exemplary reagents and methods for photo-crosslinking a gel to a surface are described in the provisional application U.S. Ser. No. 61/657,508.

This disclosure further provides a nucleic acid array. The array can include a surface having metal regions and interstitial regions having a composition that differs from the metal regions, wherein a continuous gel layer coats the surface across the metal regions and the interstitial regions, wherein nucleic acids are attached to the continuous gel layer, and wherein a greater amount of the nucleic acids are attached to portions of the gel layer that coat the metal regions than the amount of nucleic acids that attach to portions of the gel layer that coat the interstitial region.

In particular embodiments, a nucleic acid array can have a surface with (a) mask regions or metal regions, wherein individual mask regions are attached to a single (i.e. no more than one) nucleic acid template; and (b) interstitial regions, wherein a continuous gel layer coats the surface across the mask regions and the interstitial regions, wherein a plurality of nucleic acid copies of the template nucleic acid are attached to the continuous gel layer in respective clusters surrounding the metal regions. The mask regions or metal regions can have a composition that blocks transmittance of electromagnetic radiation in a first part of the electromagnetic radiation spectrum and the interstitial regions can have a composition that transmits radiation in the first part of the electromagnetic radiation spectrum.

Also provided is a nucleic acid array having a surface with mask regions having a composition that blocks transmittance of electromagnetic radiation in a first part of the electromagnetic radiation spectrum and transparent regions having a composition that transmits radiation in the first part of the electromagnetic radiation spectrum, wherein a continuous gel layer coats the surface across the mask regions and the transparent regions, wherein nucleic acids are attached to the continuous gel layer, and wherein a greater amount of the nucleic acids are attached to portions of the gel layer that coat the transparent regions than the amount of nucleic acids that are attached to portions of the gel layer that coat the mask regions.

Further provided is a nucleic acid array having a surface with mask regions having a composition that blocks transmittance of electromagnetic radiation in a first part of the electromagnetic radiation spectrum and transparent regions having a composition that transmits radiation in the first part of the electromagnetic radiation spectrum, wherein a continuous gel layer coats the surface across the mask regions and the transparent regions, wherein nucleic acids are attached to the continuous gel layer, and wherein a greater amount of the nucleic acids are attached to portions of the gel layer that coat the mask regions than the amount of nucleic acids that are attached to portions of the gel layer that coat the transparent regions.

Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; U.S. Pat. No. 7,057,026; WO 91/06678; WO 07/123744; U.S. Pat. Nos. 7,329,492; 7,211, 414; 7,315,019; 7,405,281, and US 2008/0108082, each of which is incorporated herein by reference in its entirety.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210, 891; 6,258,568 and 6,274,320, each of which is incorporated herein by reference in its entirety). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference in its entirety.

Sequencing-by-ligation reactions are also useful including, for example, those described in Shendure et al. *Science* 309:1728-1732 (2005); U.S. Pat. Nos. 5,599,675; and 5,750, 341, each of which is incorporated herein by reference in its entirety. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference in its entirety. In both sequencing-by-ligation and sequencing-by-hybridization procedures, nucleic acids that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in its entirety.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/ 0282617 A1, each of which is incorporated herein by reference in its entirety.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. No. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety.

The following examples are intended to illustrate but not limit the present invention.

Example I

Preparation and Analysis of Aluminum Oxide Patterned Flow-Cells

This example demonstrates preparation of a glass substrate having aluminum oxide metal surface regions and interstitial surface regions where the metal is not present on the glass surface. This Example also demonstrates enhancement of DNA cluster formation on the metal-coated surfaces compared to the interstitial surfaces.

Figure 1B:
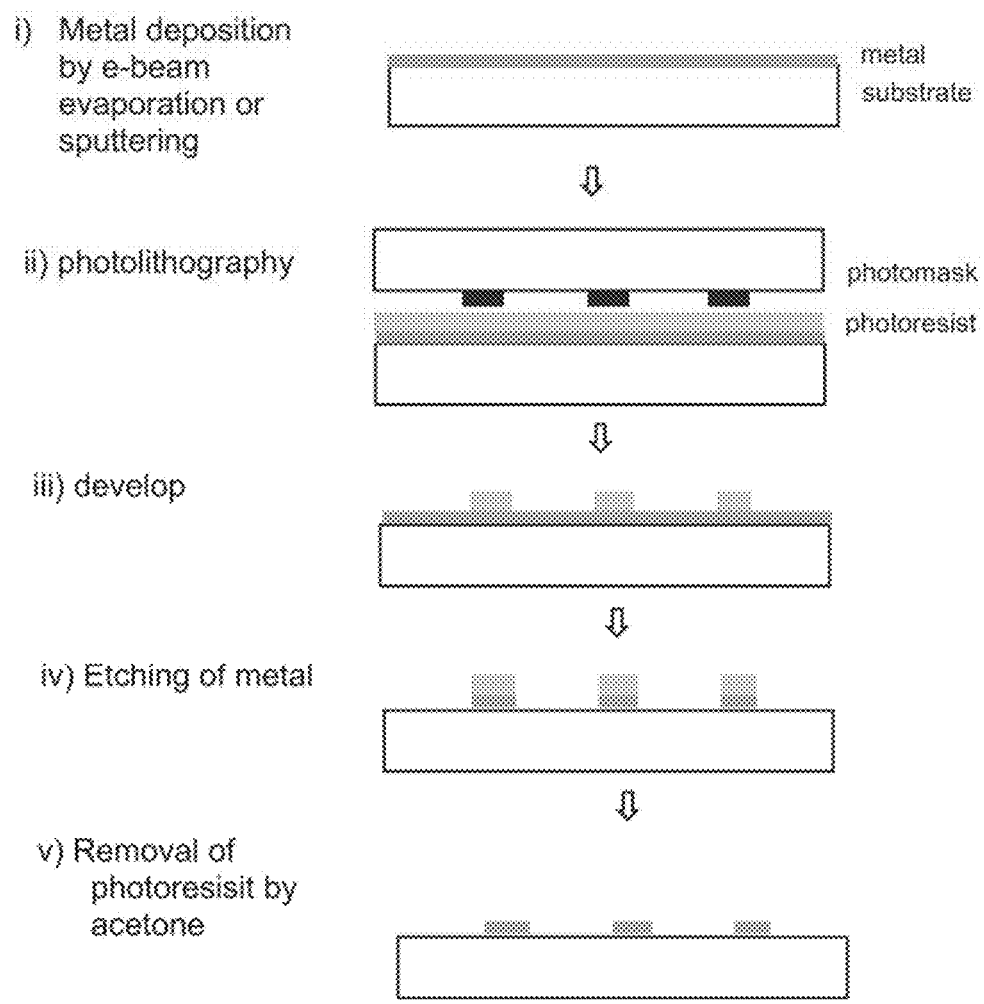

Glass flow-cells (Illumina, Inc., San Diego, CA) were coated with aluminum oxide patches as shown in FIG. 1A or 1B. Briefly, FIG. 1A shows a profile of a glass flow-cell treated to create metal patches (also referred to as metal regions) using a lift-off approach. More specifically, a photoresist layer was evenly coated over the surface of the glass flow-cell and patches of the photoresist were removed by photolithography to expose patches of the glass surface. A layer of aluminum oxide was then deposited on the surface to form a continuous thin film over the photoresist regions and glass patches. Aluminum oxide was deposited using e-beam evaporation or sputtering as set forth in Thornton, *Ann. Rev. Mater. Sci.* 7:239-60 (1977), which is incorporated herein by reference in its entirety. The photoresist layer was then removed by Acetone lift off to leave aluminum oxide patches. In the lift-off approach the transparent regions of the photomask used for photolithography corresponded to regions of the flow cell that would eventually become metal patches, whereas the mask regions of the photomask corresponded to regions of the flow cell that would eventually become interstitial regions that separate metal patches.

FIG. 1B shows a profile of a glass flow-cell treated to create metal patches using an etching approach. An aluminum oxide layer was deposited to create a metal layer on the glass surface of the flow cell, again using e-beam evaporation or sputtering. A photoresist layer was then coated over the metal layer and photolithography was carried out using a photomask to produce patches of photoresist on the metal surface. The flow cell was then treated with sodium hydroxide to etch metal that was not protected by the photoresist patches. The photoresist patches were removed with acetone leaving metal patches corresponding to regions of the metal surface that had been protected from etching by the photoresist patches. The metal patches were separated by interstitial regions where metal had been removed to expose the glass surface. In the etching approach the mask regions of the photomask used for photolithography corresponded to regions of the flow cell that would eventually become metal patches, whereas the transparent regions of the photomask corresponded to regions of the flow cell that would eventually become interstitial regions that separate metal patches.

Figure 2:
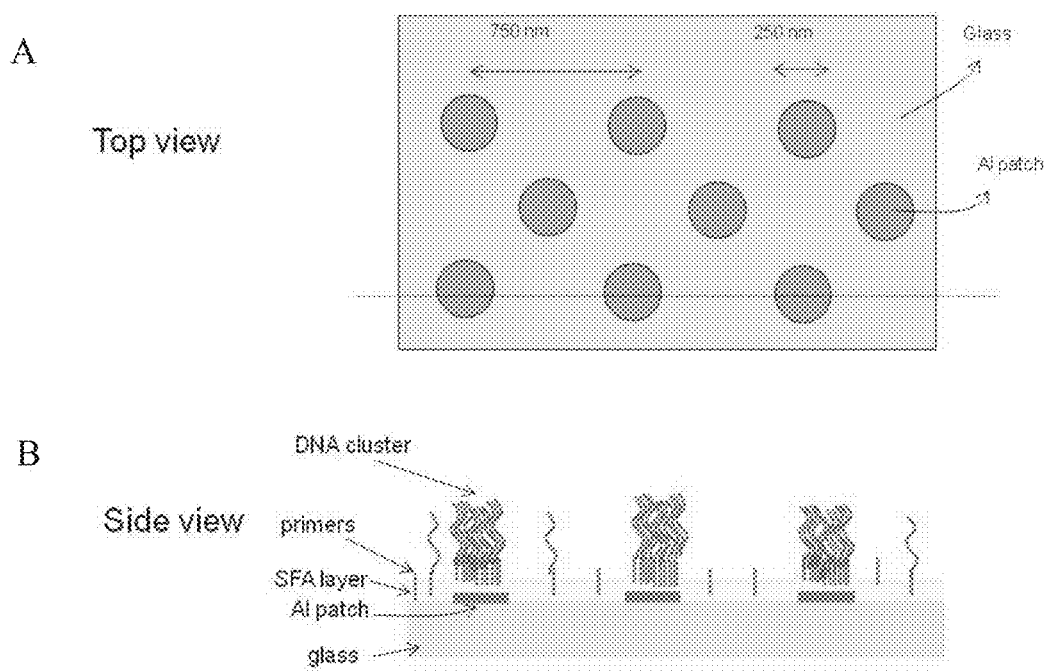
FIG. 2 shows diagrammatic representations of (A) a top view of a surface having metal regions and (B) a side view of the surface after coating with a continuous gel layer, grafting of primers and growth of DNA clusters on the primers.

The aluminum oxide patches that resulted from the above treatments were 5 to 50 nm thick, circular in shape with a diameter of about 250 nm, and surrounded by interstitial regions of glass surface such that the metal regions were separated by a pitch of 750 nm. A diagrammatic representation of the surface is shown in FIG. 2A.

The aluminum oxide-coated flow-cell was then coated with silane-free acrylamide (SFA) as described at pages 61-62 of WO 2008/093098 (which is incorporated herein in its entirety) except that the temperature for the polymerization reaction was 35° C., the reaction time was 30-40 min, the amount of TEMED used was 11 µl, and the amount of potassium persulfate used was 96 µl. Primers were grafted to the polymerized SFA as described in WO 2008/093098. DNA templates were hybridized to the primers and amplified by bridge amplification to form DNA clusters also as described in WO 2008/093098.

Surprisingly, for flow-cells prepared as described above a 3 to 10 fold increase in primer density was observed over metal patches as compared to the density of primers over interstitial regions. Similarly, a 3 to 10 fold increase in signal intensity was observed for DNA clusters formed over metal patches compared to signal detected from interstitial regions A diagrammatic representation of a flow-cell resulting from the above methods is shown in FIG. 2B. As shown in the figure an SFA polymer layer coats the flow-cell surface, covering the metal patches and interstitial glass regions as a continuous layer. The primers are attached to the SFA layer. Although primers are attached to locations throughout the SFA polymer layer, the concentration of primers is substantially higher over the aluminum oxide, metal patches than over the interstitial glass regions. Template DNA molecules form clusters primarily over the aluminum oxide metal patches, with little to no template attachment or amplification over the interstitial regions.

Figure 3:
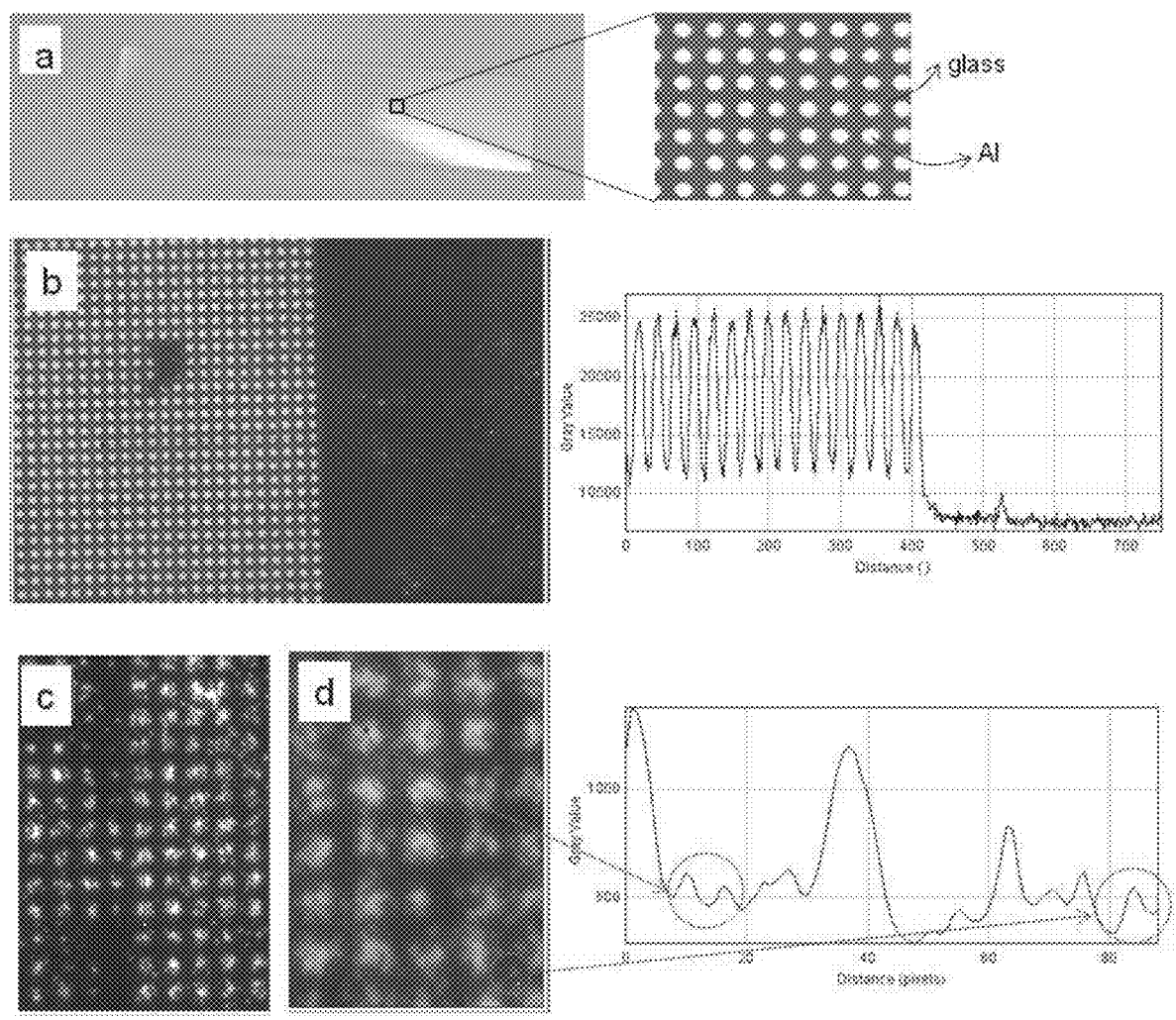
FIG. 3 shows (A) photographs of a full view for a flow-cell having a metal patterned surface and a magnified view of a portion of the surface; (B) a fluorescent image of a metal patterned surface after coating with silane-free acrylamide (SFA) polymer and grafting of primers to the SFA polymer and hybridization of fluorescent labeled probes to the primers, and a plot of grayscale vs. distance for a line measured across the surface; (C) and (D) high magnification images of DNA clusters grown on a metal patterned surface and a plot of grayscale vs. distance for a line measured across the surface.

FIG. 3 shows photographic images and related measurements for flow-cells prepared generally as set forth above (with exceptions as indicated). FIG. 3A shows a flow-cell substrate, and a magnified view of a portion thereof, after being coated with 3 micron diameter, aluminum oxide patches. FIG. 3B shows the flow-cell surface after the following treatment. The substrate having 3 micron aluminum oxide patches was coated with SFA and the SFA was then attached to primers as described above. The primers were then hybridized to probes having a Texas Red dye and excess, unhybridized probes were washed away. The hybridized probes were detected using excitation at 589 nm and emission at 615 nm. The fluorescence image in the left side panel of FIG. 3B shows a pattern of fluorescent signals from primer populations that form over the metal regions. A substantial contrast can be seen between primer patches formed over metal regions as compared to the relatively low signal produced from interstitial glass regions. This contrast is indicative of the specificity with which the primers attach to SFA at metal regions compared to SFA at interstitial glass regions. The plot of gray values vs. distance in the right side panel of FIG. 3B shows a pattern of signals from the primer regions that correlates with the diameter and pitch of the metal regions.

FIGS. 3C and 3D show magnified views of a flow-cell after patterning with 3 micron diameter aluminum oxide patches, coating with SFA polymer, grafting of primers, and performing bridge amplification to form clusters. The clusters were treated with a SYBR Green labeled intercalating agent, washed to remove non-intercalated agent and fluorescence was detected using a fluorescence microscope. The images in FIGS. 3C and 3D show that clusters formed in a regular pattern that was correlated with the pattern of metal patches on the surface. The plot of gray values vs. distance shows that although some signal was present in interstitial regions, the signal from clusters formed over metal patches was far larger.

Example II

Application of Metal Patches as Near-Field Photo-Masks

This Example describes creation of an array of nucleic acid features. A surface having metal patches separated by interstitial regions was coated with a gel and photo-cleavable nucleic acid primers were attached to the gel. Primers that attached to portions of the gel that coat interstitial regions were photo-cleaved while primers that were attached to portions of the gel that coated metallic patches were masked from photo-cleavage. The remaining patches of nucleic acid primers formed an array of features on the surface.

Figure 4:
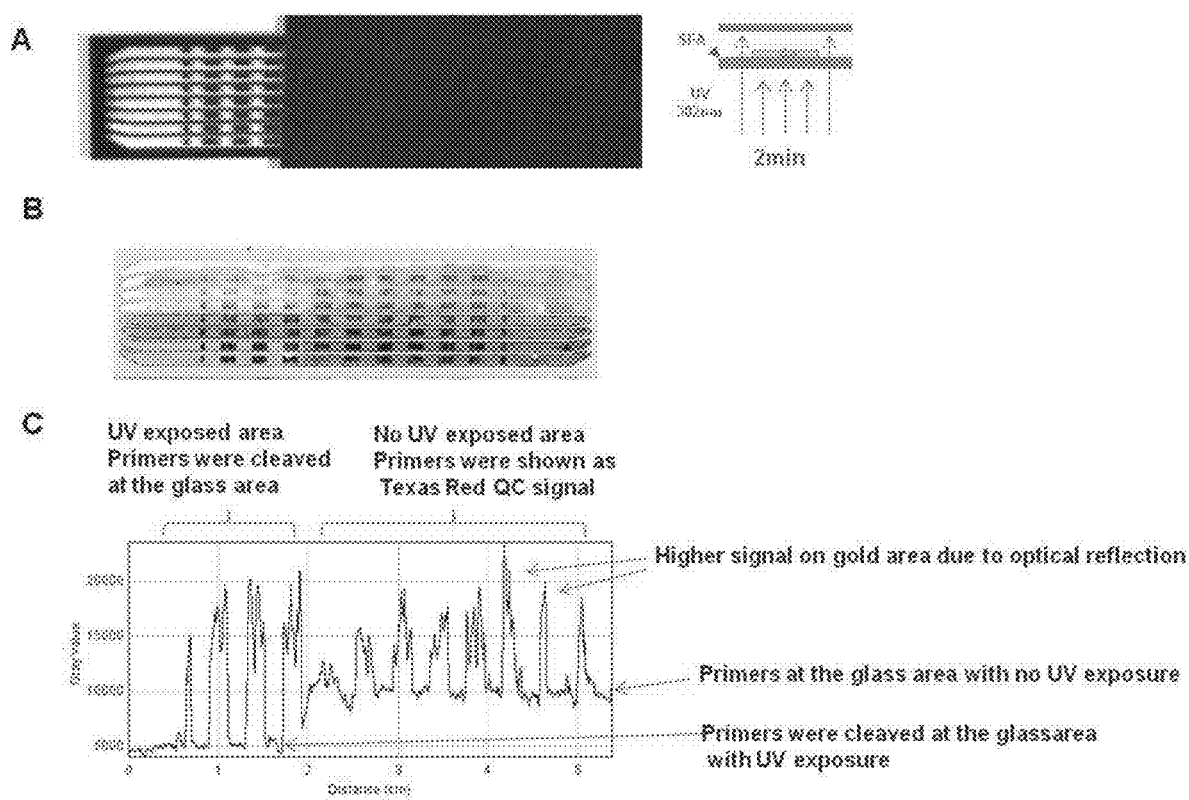
FIG. 4 shows results of selectively photo-cleaving primers at non-metal regions of a metal patterned flow-cell: (A) experimental set up for irradiating the flow-cell with UV light from the bottom of the flow-cell; (B) image of the flow-cell after UV exposure; (C) plot of grayscale vs. distance showing primer distribution for lane 8 of the flow-cell.

Glass flow-cells (Illumina, Inc., San Diego, CA) were coated with gold patches using methods set forth in Example I, except that metal deposition was carried out with gold instead of aluminum oxide. The resulting flow-cell had eight lanes each with 12 gold patches separated by glass interstitial regions. The gold-coated flow-cell was then coated with silane-free acrylamide (SFA) as described in Example I. Primers were grafted to the SFA coated flow-cell using the primer grafting methods described in Example I. The primers in lanes 1-4, 7 and 8 were grafted to the SFA layer via a nitrobenzyl UV cleavable moiety (Glenn Research, Sterling, VA). The primers in lanes 5 and 6 did not have a photo-reactive group and were therefore not UV cleavable. The flow cell is oriented in FIG. 4 such that lanes 1 through 8 are in order from top to bottom. The grafted primers were then hybridized with complementary probes having Texas Red labels.

Following hybridization of labeled probes, the flow-cell was then washed and placed over a UV light source. The flow-cell was positioned with respect to the UV (302 nm) light source such that the gold patches created a mask for primers attached over the patches while any primers attached over interstitial regions were exposed to the UV light. Furthermore, a large mask was placed between the UV source and half of the flow-cell as shown in FIG. 4A to create a UV exposed area and a control area that was not exposed to UV. UV exposure occurred for 2 minutes at room temperature. As a result of the experimental set-up, the UV exposed region of the flow-cell contained four gold patches and four interstitial regions; the non-UV exposed region of the flow-cell contained the remaining eight gold patches and eight interstitial regions.

FIG. 4B shows an image of the flow-cell following UV exposure. A plot of gray value vs. distance is shown for lane 8 of the flow-cell in FIG. 4C. As shown in the plot, the signal from the four UV-exposed interstitial regions was reduced by about 50% compared to signal from the eight non UV-exposed interstitial regions. This is indicative of photo-cleavage of the primers by UV light. The plot also shows that the signal from primers over the four UV-exposed gold patches was similar to the signal for the eight non-UV exposed gold patches. This is indicative of the gold patches providing a mask protecting the primers from photo-cleavage.

These results show that metal patches located on the surface of a substrate can form a near-field mask to radiation. Surprisingly, the near-field mask provides effective protection even from non-collimated light. As demonstrated by these results, a near-field mask can be used in combination with photo-cleavage to produce a surface having a pattern of features containing nucleic acid primers.

Example III

This example describes methods that can be used to create an array of nucleic acid features.

Figure 5:
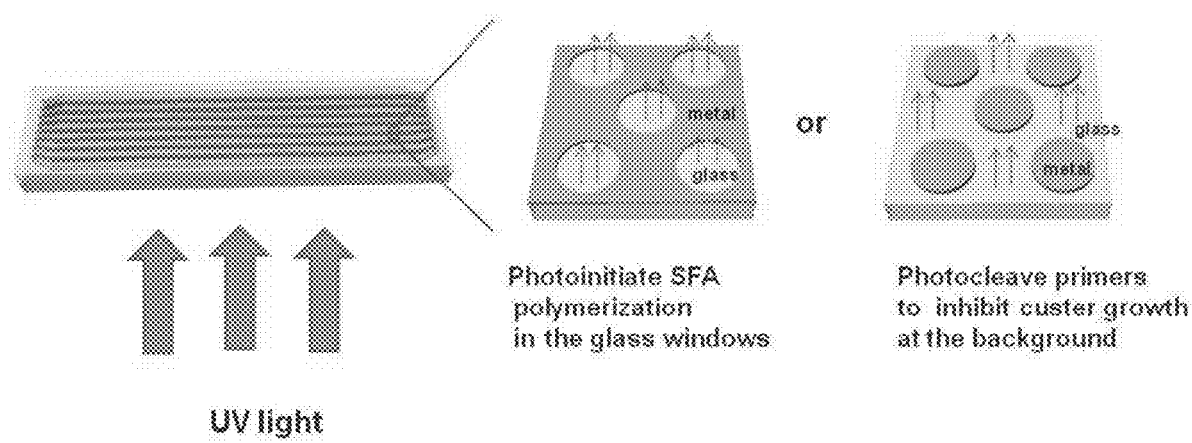
FIG. 5 shows a schematic representation of two methods for creating gel and/or nucleic acid features on a metal patterned flow-cell.

FIG. 5 provides a diagrammatic representation of two exemplary methods for creating an array of features, wherein the features contain a gel and/or nucleic acids. Generally, a flow-cell is created as described in Examples I or II or elsewhere herein. The flow-cell surface has metal regions (such as gold or aluminum oxide) separated by interstitial regions (such as glass). A gel layer, such as polymerized silane-free acrylamide (SFA), is present as a continuous coating over the flow-cell surface. The flow-cell can also optionally include primers attached to the gel layer. The flow-cell is irradiated from below, for example with UV light, such that the metal regions provide a near-field mask to block irradiation of regions of the gel that are above the metal regions, whereas regions of the gel that are located above glass interstitial regions are irradiated. If primers are attached to the gel then the metal patches provide a near-field mask to block irradiation of primers that are attached above the metal primers, whereas primers that are located above glass interstitial regions are irradiated.

In a first alternative the UV light causes polymerization of a gel. For example, as shown in FIG. 5 the UV light photo-initiates polymerization of SFA at interstitial regions and the metal regions mask polymerization. In this way an array of gel features is produced.

In a second alternative, UV light removes primers from interstitial regions. As shown in FIG. 5, the UV light photo-cleaves primers in the interstitial regions while primers that are attached above the metal regions are masked from photo-cleavage. As such an array of nucleic acid features is produced. Optionally, the primers are seeded with template nucleic acids and the template nucleic acids are amplified, for example, by bridge amplification to form an array of nucleic acid clusters.

Figure 6:
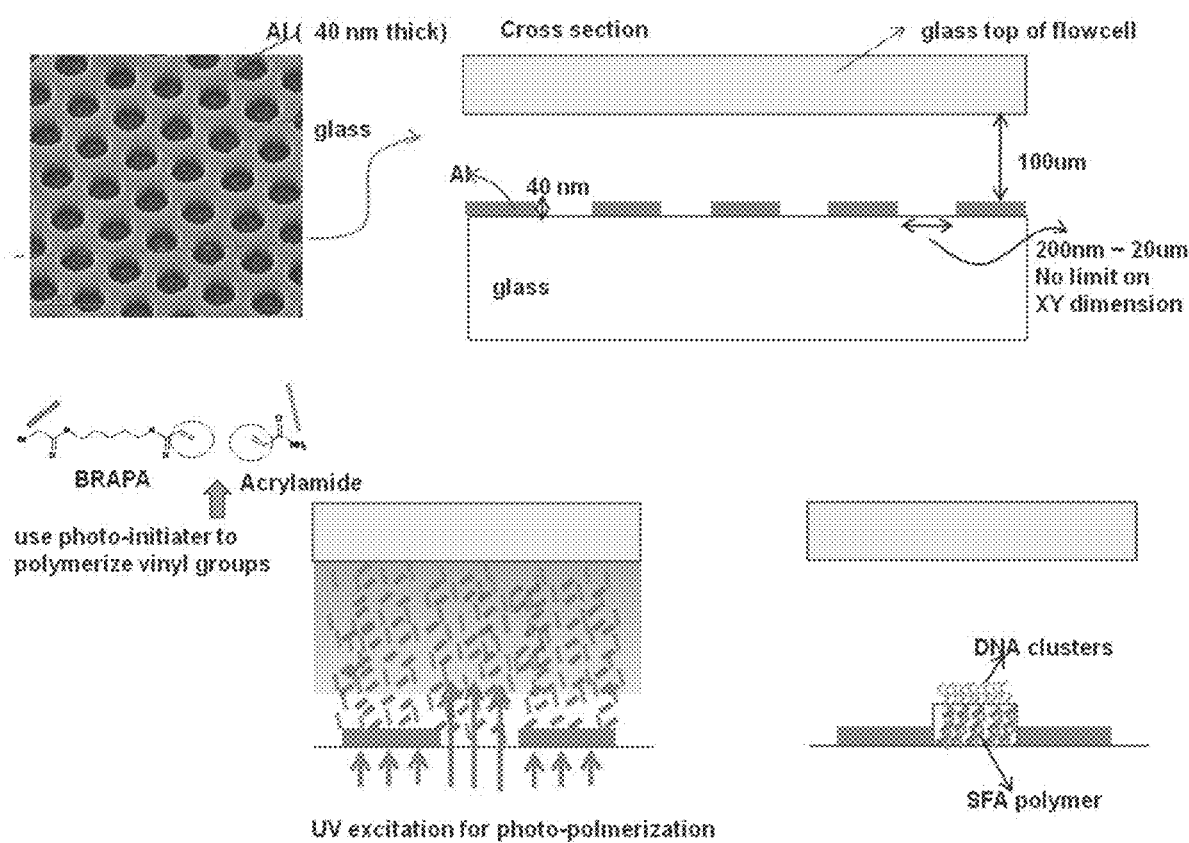
FIG. 6 shows a schematic representation of a method for photo-initiation of SFA polymerization in interstitial regions of a metal patterned surface and selective DNA cluster growth in the interstitial regions compared to metal regions.

Further details regarding the first alternative are shown in FIG. 6. The flow-cell surface is patterned to have circular glass regions surrounded by aluminum oxide. The aluminum oxide can be, for example, 40 nm thick. The glass regions have a diameter that is between 200 nm and 20 microns, but need not be limited to this range. The flow-cell has a fluidic space that is about 100 microns in height. A solution of silane-free acrylamide and BRAPA having a photo-initiator moiety such as 2,2'-Azobis[2-methyl-N-(2-hydroxyethyl) propionamide] or benzophenone is introduced to the flow-cell. The flow-cell is irradiated with UV light from below such that the metal regions provide a mask that prevents polymerization above the metal regions. However, UV light passes through the glass such that photo-induced polymerization occurs at each glass region. Thus an array of circular features is formed, each feature containing polymerized SFA. Primers are grafted to the polymerized SFA and clusters are formed at the gel features using methods set forth in Examples I or II or elsewhere herein.

Figure 7:
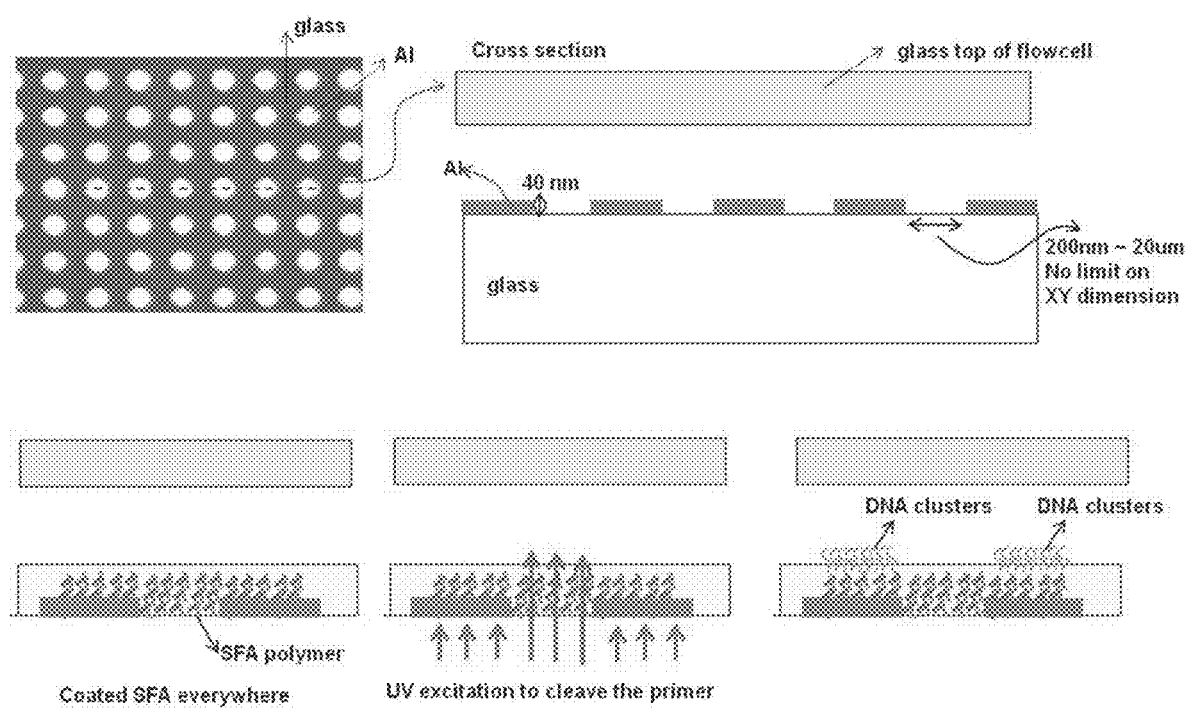
FIG. 7 shows a schematic representation of a method for photo-cleaving of primers in the interstitial regions of a metal patterned surface and selective DNA cluster growth in the metal regions compared to the interstitial regions.

Further details regarding the second alternative are shown in FIG. 7. The flow-cell surface is patterned to have circular patches of aluminum oxide metal surrounded by glass interstitial regions. The aluminum oxide can be, for example, 40 nm thick. The metal regions have a diameter that is between 200 nm and 20 microns, but need not be limited to this range. The flow-cell has a fluidic space that is about 100 microns in height. A coating of SFA polymer is formed to create a continuous layer over the surface including the metal regions and the interstitial regions as described in Example I. A primer is attached to the SFA layer via a photo-cleavable linker as described in Example II. The flow-cell is irradiated with UV light from below such that the metal regions provide a mask that prevents cleavage of primers above the metal regions. However, UV light passes through the glass such that photo-cleavage of primers occurs above each glass region. Thus an array of nucleic acid features is formed, each feature containing a population of attached primers. Clusters are formed at the primer features using methods set forth in Examples I or II or elsewhere herein.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of making an analyte array, comprising:
   (a) providing a surface comprising mask regions and transparent regions, the mask regions having a composition that blocks transmittance of radiation in a first part of the electromagnetic spectrum and transparent regions having a composition that transmits radiation in the first part of the electromagnetic spectrum, wherein a continuous gel layer coats the surface across the mask regions and the transparent regions;
   (b) contacting the continuous gel layer with a fluid comprising a population of different analytes under conditions wherein analytes from the population become attached to the gel layer and wherein a first subpopulation of the analytes attach to portions of the gel layer that coat the mask regions and a second subpopulation of the analytes attach to portions of the gel layer that coat the transparent regions; and
   (c) irradiating the surface with radiation in the first part of the electromagnetic spectrum, thereby selectively modifying the analytes of one of the subpopulations compared to the analytes of the other subpopulation, wherein the selectively modifying the analytes of the one of the subpopulations involves:
      attaching two or more analytes of the one of the subpopulations to each other;
      removing an optical label from the one of the subpopulations of analytes; or
      attaching the optical label to the one of the subpopulations of analytes.

2. The method of claim 1, further comprising removing the mask regions from the surface under conditions wherein the analytes remain attached to the gel layer on the surface.

3. The method of claim 1, wherein the selectively modifying further involves selectively removing the analytes of the second subpopulation compared to the analytes of the first subpopulation.

4. The method of claim 3, wherein the removing comprises photo-cleaving the analytes of the second subpopulation using radiation in the first part of the electromagnetic radiation spectrum.

5. The method of claim 4, wherein the analytes of the first subpopulation are masked from the photo-cleaving by the mask regions.

6. The method of claim 1, wherein the analytes comprise nucleic acids.

7. The method of claim 6, further comprising amplifying the nucleic acids on the portions of the gel layer that coat the mask regions.

8. The method of claim 7, further comprising removing the mask regions from the surface under conditions wherein the products of the amplifying of the nucleic acids remain attached to the gel layer.

9. The method of claim 6, wherein the contacting occurs under conditions wherein a uniform concentration of the nucleic acids contacts the portions of the continuous gel layer that coat the mask regions and the transparent regions.

10. The method of claim 6, wherein the continuous gel layer comprises a continuous polyacrylamide layer.

11. The method of claim 6, wherein the nucleic acids that attach to the portions of the gel layer that coat the mask regions have the same sequence.

12. The method of claim 11, wherein the nucleic acids that attach to the portions of the gel layer that coat the mask regions comprise a pair of primers.

13. The method of claim 1, wherein the transparent regions comprise glass, plastic or silica.

14. The method of claim 1, wherein the surface of the mask regions comprise metal, thereby forming metal regions on the surface.

15. The method of claim 1, wherein the surface is located in a flow-cell.

16. The method of claim 1, wherein step (c) comprises selectively modifying the analytes of the second subpopulation compared to the analytes of the first subpopulation.

17. The method of claim 16, wherein the selectively modifying comprises photo-chemically activating the analytes of the second subpopulation.

18. The method of claim 1, wherein step (c) comprises selectively modifying the analytes of the first subpopulation compared to the analytes of the second subpopulation.

19. A method of making a nucleic acid array, comprising:
   (a) providing a surface comprising metal regions and interstitial regions, the interstitial regions having a composition that differs from the metal regions, wherein a continuous gel layer coats the surface across the metal regions and the interstitial regions;
   (b) contacting the continuous gel layer with a fluid comprising analytes; and
   (c) selectively modifying the portions of the gel layer that coat the interstitial regions compared to the portions of the gel layer that coat the metal regions, wherein the selectively modifying the portions of the gel layer that coat the interstitial regions involves:
      attaching two or more nucleic acids to one another at the interstitial regions;
      removing an optical label from a nucleic acid at the interstitial regions; or
      attaching the optical label to the nucleic acid at the interstitial regions.

* * * * *